United States Patent [19]
Norgard

[11] Patent Number: 5,681,934
[45] Date of Patent: Oct. 28, 1997

[54] **47-KILODALTON ANTIGEN OF *TREPONEMA PALLIDUM***

[75] Inventor: Michael V. Norgard, Plano, Tex.

[73] Assignee: Board of Regents, The University of Texas System, Austin, Tex.

[21] Appl. No.: 226,486

[22] Filed: Apr. 12, 1994

Related U.S. Application Data

[63] Continuation-in-part of Ser. No. 940,245, Aug. 31, 1992, Pat. No. 5,350,842, and Ser. No. 658,630, Feb. 21, 1991, abandoned, each is a continuation-in-part of Ser. No.235, 351, Aug. 23, 1988, abandoned, which is a continuation of Ser. No. 913,724, Sep. 30, 1986, Pat. No. 4,868,118.

[51] Int. Cl.$^6$ .......................... C07K 14/20; C12N 15/31
[52] U.S. Cl. ........................ 530/403; 530/324; 530/350; 435/69.1; 435/69.3; 435/172.3; 435/252.3; 435/320.1; 536/23.1; 536/23.7
[58] Field of Search ........................................ 530/403, 350, 530/324, 326, 327, 328; 435/69.3, 69.1, 172.3, 320.1, 252.3, 252.1; 536/23.1, 23.7

[56] References Cited

U.S. PATENT DOCUMENTS

| | | | |
|---|---|---|---|
| 4,288,426 | 9/1981 | Stevens | 435/7.36 |
| 4,514,498 | 4/1985 | Kettman et al. | 530/388.4 |
| 4,554,101 | 11/1985 | Hopp | 530/324 |
| 4,740,467 | 4/1988 | Kettman et al. | 435/7.36 |
| 4,868,118 | 9/1989 | Norgard | 435/252.33 |
| 4,959,314 | 9/1990 | Mark et al. | 435/69.1 |

FOREIGN PATENT DOCUMENTS

| | | |
|---|---|---|
| 1262333 | 10/1989 | Canada. |
| PCT/US83/01718 | 5/1984 | WIPO. |
| PCT/US87/02403 | 4/1988 | WIPO. |

OTHER PUBLICATIONS

Alderete et al., "Surface Characterization of Virulent *Treponema pallidum*", *Infect. Immun.*, 30(3):814–823, 1980, published in USA.
Baker et al., "Inactivation of Suppressor T-Cell Activity by Nontoxic Monophosphoryl Lipid A", *Infect. Immun.*, 56 (5):1076–1083 1988 published in USA.
Baker–Zander et al., "Molecular Basis of Immunological Cross-Reactivity Between *Treponema pallidum* and *Treponema pertenue*", *Infect. Immun.*, 42 (2):634–638, 1983, published in USA.
Baker–Zander et al., "Antigenic Cross-Reactivity Between *Treponema pallidum* and Other Pathogenic Members of the Family Spirochaetaceae", *Infect. Immun.*, 46(1):116–121, 1984, published in USA.
Baker–Zander et al., "Antigens of *Treponema pallidum* Recognized by IgG and IgM Antibodies During Syphilis in Humans", *J. Infect. Dis.*, 151(2):264–272, 1985, published in USA.

Bishop et al., "Humoral Immunity in Experimental Syphilis", *J. Immunol.*, 117(1):197–207, 1976, published in USA.
Chase et al., "Effect of Monophosphoryl Lipid A on Host Resistance to Bacterial Infection", *Infect. Immun.* 53:711–712, 1986 published in USA.
Bordier, "Phase Separation of Integral Membrane Proteins in Triton X–114 Solution", *J. Biolog. Chem.*, 256(4):1604–1607, 1981, published in USA.
Coates et al., "Serospecifity of a 18,000 Molecular Weight *Treponema pallidum* Antigen Cloned and Expressed in *Escherichia coli*", Abst. 85th Ann. Mtg. Amer. Soc. Microbiol., Abstract #C–29, p. 304, published in USA.
Cunningham et al., "Identification of *Treponema pallidum* Outer Envelope Components by Triton X–114 (TX–114) Phase Partition", *Mol. Cell. Biol.*, Abstract H–103, p. 112, published in USA.
Chamberlain et al., "Genetic and Physicochemical Characterization of the Recombinant DNA–Derived 47–Kilodalton Surface Immunogen of *Treponema pallidum* subsp. *pallidum*", *Infect. Immun.*, 56(1):71–78, 1988, published in USA.

(List continued on next page.)

*Primary Examiner*—John L. LeGuyader
*Attorney, Agent, or Firm*—Arnold, White & Durkee

[57] ABSTRACT

The present disclosure provides the complete primary amino acid, and underlying DNA, sequence for the 47-kilodalton membrane immunogen of *Treponema pallidum*, subsp. pallidum. The sequence was obtained by using a combined strategy of DNA sequencing of the cloned gene as well as confirmatory N-terminal amino acid sequencing of the native antigen. An open reading frame corresponding to the 47-kDa antigen was comprised of 434 amino acid codons. This open reading frame contained a typical 19 amino acid hydrophobic leader peptide flanked by a consensus sequence of Val-Val-Gly-Cys for signal peptidase II, the lipoprotein-specific signal peptidase of prokaryotes. The molecular weight of the mature molecule, excluding modification, is 45,756. Also disclosed are methods for preparing variant and mutant molecules having biologically similar attributes, as well as methods for preparing particular antigenic/immunogenic subportions of the 47-kDa protein. In particular aspects, antigenic/immunogenic subportions are identified by hydrophilicity analysis of the protein sequence. The 47-kDa antigen and antigenic subportions of the present invention can be used both as antigens in the detection of clinical materials having anti-47-kDa. Antibodies therein for reliable detection of *T. pallidum* infection, as well as in the preparation of vaccines for use in connection with promoting an immune state in vaccinated individuals. Also disclosed are DNA sequences which may be useful both in the preparation of second generation antigens, and as hybridization probes in the detection of pathogenic *T. pallidum* in clinical samples. Particular methods and embodiments are also disclosed which allow greatly improved recombinant DNA production of the 47-kDa antigen, including placement of the gene under the control of the T7 RNA polymerase promoter.

11 Claims, 4 Drawing Sheets

OTHER PUBLICATIONS

Clemetson et al., "Distribution of Platelet Glycoproteins and Phosphoproteins in Hydrophobic and Hydrophilic Phases in Triton X-114 Phase Partition", *Biochimica et Biophysica Acta,* 778:463-469, 1984, published in Europe.

Cunningham et al., "A *T. pallidum* Gene Cluster Encodes Five Polypeptides Identified in the Outer Membranes of Recombinant *E. coli* Cells", Abstract D-149, p. 90, 1986, published in USA.

Clyde et al., "Antigenic Determinants of the Attachment Protein of *Mycoplasma pneumoniae* Shared by Other Pathogenic Mycoplasma Species", *Infect. Immun.,* 51(2):690-692, 1986, published in USA.

Etges et al., "The Major Surface Protein of Leishmania Promastigotes Is Anchored in the Membrane by a Myristic Acid-Labeled Phospholipid", *The EMBO Journal,* 3:597-601, 1986, published in Great Britain.

Fehniger et al., "Purification and Characterization of a Cloned Protease-Resistant *Treponema pallidum*-Specific Antigen", *Infect. Immun.,* 46 (2):598-607, 1984, published in USA.

Fehniger et al., "Identification and Partial Characterization of a Cloned 38 kd Membrane Protein Antigen from *Treponema pallidum*", Abst. 85th Ann. Mtg. Amer. Soc. Microbiol., Abstract #B-156, p. 44, 1985, published in USA.

Fehniger et al., "Native Surface Association of a Recombinant 38-Kilodalton *Treponema pallidum* Antigen Isolated from the *Escherichia coli* Outer Membrane", *Infect Immun.,* 52:586-593, 1986 published in USA.

Peterson et al., "Cloning of the Structural Gene for a Highly Immunogenic Outer Envelope Protein of *Treponema pallidum*", Abst. Ann. Mtg., Abstract B-140, p. 47, 1986, published in USA.

Hanff et al., "Humoral Immune Response in Human Syphilis to Polypeptides of *Treponema pallidum*", *J. Immunol.,* 129:1287-1291, 1982, published in USA.

Hansen et al., "Genetic Characterization and Partial Sequence Determination of a *Treponema pallidum* Operon Expressing Two Immunogenic Membrane Proteins in *Escherichia coli*", *J. Bacteriol.,* 162(3):1227-1237, 1985, published in USA.

Hindersson et al., "Immunochemical Characterization and Purification of *Treponema pallidum* Antigen TpD Expressed by *Escherichia coli* K12", *Sexually Transmitted Disease,* Oct.-Dec., pp. 237-244, 1986, published in USA.

Hook et al., "Detection of *Treponema pallidum* in Lesion Exudate with a Pathogen-Specific Monoclonal Antibody", *J. Clin. Microbiol.,* 22(2):241-244, 1985, published in USA.

Jones et al., "A Monoclonal Antibody Directed Against a 47,000d Surface Antigen of *Treponema pallidum,* has MHA-TP, TPI and Complement-Mediated Neutralizing Activity", Abst. Ann. Mtg., Abstract B173, p. 46, 1984, published in USA.

Jones et al., "Monoclonal Antibody with Hemagglutination, Immobilization, and Neutralization Activities Defines an Immunodominant, 47,000 Mol Wt, Surface-Exposed Immunogen of *Treponema pallidum*", *J. Exp. Med.,* 160:1404-1420, 1984, published in USA.

Kersten et al., "Incorporation of the Major Outer Membrane Protein of *Neisseria gonorrhoeae* in Saponin-Lipid Complexes (Iscoms): Chemical Analysis, Some Structural Features, and Comparison of Their Immunogenicity with Three Other Antigen Delivery Systems", *Infect. Immunol.,* 56:432-438, 1988, published in USA.

Lukehart et al., "Identification of *Treponema pallidum* Antigens: Comparison with a Nonpathogenic Treponeme", *J. Immunol.,* 129:833-838, 1982, published in USA.

Lukehart et al., "Characterization of Monoclonal Antibodies to *Treponema pallidum*", *J. Immunol.,* 134(1):585-592, 1985, published in USA.

Lukehart et al., "Characterization of the Humoral Immune Response of the Rabbit to Antigens of *Treponema pallidum* after Experimental Infection and Therapy", *Sex. Trans. Dis.,* Jan.-Mar., pp. 9-15, 1986, published in USA.

Marchitto et al., "Monoclonal Antibody Analysis of Specific Antigenic Similarities Among Pathogenic *Treponema pallidum* Subspecies", *Infect. Immun.,* 45:660-666, 1984, published in USA.

Marchitto et al., "Molecular Specificities of Monoclonal Antibodies Directed Against Virulent *Treponema pallidum*", *Infect. Immun.,* 51(1):168-176, 1986, published in USA.

Moseley et al., "Medical Microbiology: Detection of Enterotoxigenic *Escherichia coli* by DNA Colony Hybridization", *J. Infect. Dis.,* 142(6):892-898, 1980, published in USA.

Moskophidis et al., "Molecular Analysis of Immunoglobulins M and G Immune Response to Protein Antigens of *Treponema pallidum* in Human Syphilis", *Infect. Immun.,* 43(1):127-132, 1984, published in USA.

Norgard, "Rapid and Simple Removal of Contaminating RNA from Plasmid DNA without the Use of RNase", *Anal. Biochem.,* 113:34-42, 1981, published in USA.

Norgard et al., "Plasmid DNA in *Treponema pallidum* (Nichols): Potential for Antibiotic Resistance by Syphilis Bacteria", *Science,* 213:553-555, 1981, published in USA.

Norgard et al., "Cloning and Expression of *Treponema pallidum* (Nichols) Antigen Genes in *Escherichia coli*" *Infect. Immun.,* 42(2):435-445, 1983 published in USA.

Norgard et al., "Sensitivity and Specificity of Monoclonal Antibodies Directed Against Antigenic Determinants of *Treponema pallidum* Nichols in the Diagnosis of Syphilis", *J. Clin. Microbiol.,* 20(4).:711-717, 1984, published in USA.

Norgard et al., "Cloning and Expression of the Major 47-Kilodalton Surface Immunogen of *Treponema pallidum* in *Escherichia coli*", *Infect. Immun.,* 54(2):500-506, 1986, published in USA.

Norris et al., "Antigenic Complexity of *Treponema pallidum*: Antigenicity and Surface Localization of Major Polypeptides", *J. Immuno.,* 133(5):2686-2692, 1984, published in USA.

Penn et al., "The Outer Membrane of *Treponema pallidum*: Biological Significance and Biochemical Properties", *J. Gen. Microbiol.,* 131:2349-2357, 1985, published in Europe.

Peterson et al., "Isolation of a *Treponema pallidum* Gene Encoding Immunodominant Outer Envelope Protein P6, Which Reacts with Sera from Patients at Different Stages of Syphilis", *J. Exp. Med.,* 164:1160-1170, 1986, published in USA.

Pryde, "Triton X-114: A Detergent That Has Come in from the Cold", *Trends in Biochemical Sciences,* II:160-163, 1986, published in the Netherlands.

Radolf et al., "Identification and Localization of Integral Membrane Proteins of Virulent *Treponema pallidum* subsp. *pallidum* by Phase Partitioning with the Nonionic Detergent Triton X-114", *Infect. Immun.,* 56(2):490-498, 1988, published in USA.

Radolf et al., "Pathogen Specificity of *Treponema pallidum* subsp. *pallidum* Integral Membrane Proteins Identified by Phase Partitioning with Triton X–114", *Infect. Immun.*, 56(7):1825–1828, 1988, published in USA.

Radolf et al., "Serodiagnosis of Syphilis by Enzyme–Linked Immunosorbent Assay with Purified Recombinant *Treponema pallidum* Antigen 4D", *J. Infect. Dis.*, 153 (6):1023–1027, 1986, published in USA.

Richards et al., "Liposomes, Lipid A, and Aluminum Hydroxide Enhance the Immune Response to a Synthetic Malaria Sporozoite Antigen", *Infect. Immun.*, 56:682–686, 1988, published in USA.

Robertson et al., "Murine Monoclonal Antibodies Specific for Virulent *Treponema pallidum* (Nichols)", *Infect. Immun.*, 36(3):1076–1085, 1982, published in USA.

Rodgers et al., "Serospecificity of a 37,000 Molecular Weight *Treponema pallidum* Antigen Cloned and Expressed in *Escherichia coli*", Abst. 85th Ann. Mtg. Amer. Soc. Microbiol., Abstract #C–30, p. 305, 1985, published in USA.

Rodgers et al., "Serological Characterization and Gene Localization of an *Escherichia coli*–Expressed 37–Kilodalton *Treponema pallidum* Antigen", *Infect. Immun.*, 53(1):16–25, 1986, published in USA.

Stamm et al., "Expression of *Treponema pallidum* Antigens in *Escherichia coli* K–12", *Infect. Immun.*, 36(3):1238–1241, 1982, published in USA.

Stamm et al., "Identification and Preliminary Characterization of *Treponema pallidum* Protein Antigens Expressed in *Escherichia coli*", *Infect. Immun.*, 41(2):709–721, 1983, published in USA.

Strugnell et al., "Development of Increased Serum Immunoblot Reactivity against a 45,000–Dalton Polypeptide of *Treponema pallidum* (Nichols) Correlates with Establishment of Chancre Immunity in Syphilitic Rabbits", *Infect. Immun.*, 51(3):957–960, 1986, published in USA.

Swancutt et al., "Monoclonal Antibody Selection and Analysis of a Recombinant DNA–Derived Surface Immunogen of *Treponema pallidum* Expressed in *Escherichia coli*", *Infect. Immun.*, 52:110–119, 1986, published in USA.

Thornburg et al., "Comparison of Major Protein Antigens and Protein Profiles of *Treponema pallidum* and *Treponema pertenue*", *Infect. Immun.*, 42(2):623–627, 1983, published in USA.

Thornburg et al., "Monoclonal Antibodies to *Treponema pallidum*: Recognition of a Major Polypeptide Antigen", *Genitourin. Med.*, 61:1–6, 1985, published in Europe.

Van De Donk et al., "Monoclonal Antibodies to *Treponema pallidum*", *Develop. Biol. Standard.*, 57:107–111, 1984, published in the Netherlands.

Van Eijk et al., "Molecular Characterization of *Treponema pallidum* Proteins Responsible for the Human Immune Response to Syphilis", *Antonie van Leeuwenhoek*, 48:486–487, 1982, published in the Netherlands.

Van Embden et al., "Molecular Cloning and Expression of *Treponema pallidum* DNA in *Escherichia coli* K–12", *Infect. Immun.*, 42(1):187–196, 1983, published in USA.

Van De Donk et al., "Monoclonal Antibodies to *Treponema pallidum* and Their Use for the Characterization of Recombinant DNA Clones", *Innovations and Biotechnology*, pp. 267–273, 1984, published in the Netherlands.

Walfield et al., "Expression of *Treponema pallidum* Antigens in *Escherichia coli*", *Science*, 216:522–523, 1982, published in USA.

Young et al., "Dissection of *Mycobacterium tuberculosis* Antigens Using Recombinant DNA", *Proc. Natl. Acad. Sci. USA*, 82:2583–2587, 1985, published in USA.

Dallas et al., "Identification and Purification of a Recombinant *Treponema pallidum* Membrane Protein Antigen Expressed in *Escherichia coli*", *Infect. Immun.*, 55(5):1106–1115, 1987, published in USA.

Peterson et al., "Cloning of the Gene Encoding a Major Surface Polypeptide of *Treponema pallidum* That Reacts Strongly with Sera from Syphilis Patients", *J. Cell. Biochem.*, UCLA Symposia on Molecular & Cellular Biology, Abst. 15th Ann. Mtg., Abstract C105, p. 151, 1986, published in USA.

Hill et al., "Synthetic Oligodeoxyribonucleotide Probes for Detecting Heat–Stable Enterotoxin–Producing *Escherichia coli* by DNA Colony Hybridization", *Appl. Environ. Microbiol.*, 50(5):1187–1191, 1985, published in USA.

Wallace et al., "Oligonucleotide Probes for the Screening of Recombinant DNA Libraries", *Methods. Enzymol.*, 152:432–442, 1987, published in USA.

Geysen et al. PNAS 81;3998–4002 1984.

Palfreyman et al. 75:383–39, 1984, J. Immunol. Methods.

Walfield et al Science 216:522–533, 1982.

Mariahs et al. Molecular Cloning: a Laboratory Manual, 1982, Cold Spring Harbor Laboratory, CSH, N.Y., pp. 228, 412, 413, 422.

Stryer, "Biochemistry", Freeman & Co., N.Y., 1975, pp. 21–27.

Stryer, "Biochemistry", Freeman & Co., N.Y. pp. 107 & 120–123, 1988.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 1377 base pairs
( B ) TYPE: nucleic acid
( C ) STRANDEDNESS: double
( D ) TOPOLOGY: linear ( x i ) SEQUENCE DESCRIPTION: SEQ ID NO:1:

```
CTGCAGGGGG  GGGGGGGGGG  CCCTCTATAC  GGAGGTGTAA  TCGTGAAAGT  GAAATACGCA    60
CTACTTTCTG  CCGGAGCGCT  GCAGTTGTTG  GTTGTAGGCT  GTGGCTCGTC  TCATCATGAG   120
ACGCACTATG  GCTATGCGAC  GCTAAGCTAT  GCGGACTACT  GGGCCGGGGA  GTTGGGGCAG   180
AGTAGGGACG  TGCTTTTGGC  GGGTAATGCC  GAGGCGGACC  GCGCGGGGGA  TCTCGACGCA   240
GGCATGTTCG  ATGCAGTTTC  TCGCGCAACC  CACGGGCATG  GCGCGTTCCG  TCAGCAATTT   300
CAGTACGCGG  TTGAGGTATT  GGGCGAAAAG  GTTCTCTCGA  AGCAGGAGAC  CGAAGACAGC   360
AGGGGAAGAA  AAAAGTGGGA  GTACGAGACT  GACCCAAGCG  TTACTAAGAT  GGTGCGTGCC   420
TCTGCGTCAT  TTCAGGATTT  GGGAGAGGAC  GGGGAGATTA  AGTTTGAAGC  AGTCGAGGGT   480
GCAGTAGCGT  TGGCGGATCG  CGCGAGTTCC  TTCATGGTTG  ACAGCGAGGA  ATACAAGATT   540
ACGAACGTAA  AGGTTCACGG  TATGAAGTTT  GTCCCAGTTG  CGGTTCCTCA  TGAATTAAAA   600
GGGATTGCAA  AGGAGAAGTT  TCACTTCGTG  GAAGACTCCC  GCGTTACGGA  GAATACCAAC   660
GGCCTTAAGA  CAATGCTCAC  TGAGGATAGT  TTTTCTGCAC  GTAAGGTAAG  CAGCATGGAG   720
AGCCCGCACG  ACCTTGTGGT  AGACACGGTG  GGTACCGTCT  ACCACAGCCG  TTTTGGTTCG   780
GACGCAGAGG  CTTCTGTGAT  GCTGAAAAGG  GCTGATGGCT  CTGAGCTGTC  GCACCGTGAG   840
TTCATCGACT  ATGTGATGAA  CTTCAACACG  GTCCGCTACG  ACTACTACGG  TGATGACGCG   900
AGCTACACCA  ATCTGATGGC  GAGTTATGGC  ACCAAGCACT  CTGCTGACTC  CTGGTGGAAG   960
```

-continued

```
ACAGGAAGAG TGCCCCGCAT TTCGTGTGGT ATCAACTATG GGTTCGATCG GTTTAAAGGT      1020

TCAGGGCCGG GATACTACAG GCTGACTTTG ATTGCGAACG GGTATAGGGA CGTAGTTGCT      1080

GATGTGCGCT TCCTTCCCAA GTACGAGGGG AACATCGATA TTGGGTTGAA GGGGAAGGTG      1140

CTGACCATAG GGGGCGCGGA CGCGGAGACT CTGATGGATG CTGCAGTTGA CGTGTTTGCC      1200

GATGGACAGC CTAAGCTTGT CAGCGATCAA GCGGTGAGCT TGGGGCAGAA TGTCCTCTCT      1260

GCGGATTTCA CTCCCGGCAC TGAGTACACG GTTGAGGTTA GGTTCAAGGA ATTCGGTTCT      1320

GTGCGTGCGA AGGTAGTGGC CCAGTAGAAG AGGGGTGTCC TATCCCGTGT GTCTTAA        1377
```

(2) INFORMATION FOR SEQ ID NO:2:

(i) SEQUENCE CHARACTERISTICS:
        (A) LENGTH: 443 amino acids
        (B) TYPE: amino acid
        (C) STRANDEDNESS: single
        (D) TOPOLOGY: linear (xi) SEQUENCE DESCRIPTION: SEQ ID NO:2:

```
Val Lys Val Lys Tyr Ala Leu Leu Ser Ala Gly Ala Leu Gln Leu Leu
  1               5                  10                  15

Val Val Gly Cys Gly Ser Ser His His Glu Thr His Tyr Gly Tyr Ala
                 20                  25                  30

Thr Leu Ser Tyr Ala Asp Tyr Trp Ala Gly Glu Leu Gly Gln Ser Arg
             35                  40                  45

Asp Val Leu Leu Ala Gly Asn Ala Glu Ala Asp Arg Ala Gly Asp Leu
         50                  55                  60

Asp Ala Gly Met Phe Asp Ala Val Ser Arg Ala Thr His Gly His Gly
 65                  70                  75                  80

Ala Phe Arg Gln Gln Phe Gln Tyr Ala Val Glu Val Leu Gly Glu Lys
                 85                  90                  95

Val Leu Ser Lys Gln Glu Thr Glu Asp Ser Arg Gly Arg Lys Lys Trp
                100                 105                 110

Glu Tyr Glu Thr Asp Pro Ser Val Thr Lys Met Val Arg Ala Ser Ala
            115                 120                 125

Ser Phe Gln Asp Leu Gly Glu Asp Gly Glu Ile Lys Phe Glu Ala Val
        130                 135                 140

Glu Gly Ala Val Ala Leu Ala Asp Arg Ala Ser Ser Phe Met Val Asp
145                 150                 155                 160

Ser Glu Glu Tyr Lys Ile Thr Asn Val Lys Val His Gly Met Lys Phe
                165                 170                 175

Val Pro Val Ala Val Pro His Glu Leu Lys Gly Ile Ala Lys Glu Lys
                180                 185                 190

Phe His Phe Val Glu Asp Ser Arg Val Thr Glu Asn Thr Asn Gly Leu
            195                 200                 205

Lys Thr Met Leu Thr Glu Asp Ser Phe Ser Ala Arg Lys Val Ser Ser
        210                 215                 220

Met Glu Ser Pro His Asp Leu Val Val Asp Thr Val Gly Thr Val Tyr
225                 230                 235                 240

His Ser Arg Phe Gly Ser Asp Ala Glu Ala Ser Val Met Leu Lys Arg
                245                 250                 255

Ala Asp Gly Ser Glu Leu Ser His Arg Glu Phe Ile Asp Tyr Val Met
                260                 265                 270

Asn Phe Asn Thr Val Arg Tyr Asp Tyr Tyr Gly Asp Asp Ala Ser Tyr
            275                 280                 285
```

-continued

```
Thr  Asn  Leu  Met  Ala  Ser  Tyr  Gly  Thr  Lys  His  Ser  Ala  Asp  Ser  Trp
     290                 295                     300

Trp  Lys  Thr  Gly  Arg  Val  Pro  Arg  Ile  Ser  Cys  Gly  Ile  Asn  Tyr  Gly
305                      310                     315                          320

Phe  Asp  Arg  Phe  Lys  Gly  Ser  Gly  Pro  Gly  Tyr  Tyr  Arg  Leu  Thr  Leu
               325                          330                          335

Ile  Ala  Asn  Gly  Tyr  Arg  Asp  Val  Val  Ala  Asp  Val  Arg  Phe  Leu  Pro
               340                      345                          350

Lys  Tyr  Glu  Gly  Asn  Ile  Asp  Ile  Gly  Leu  Lys  Gly  Lys  Val  Leu  Thr
          355                      360                     365

Ile  Gly  Gly  Ala  Asp  Ala  Glu  Thr  Leu  Met  Asp  Ala  Ala  Val  Asp  Val
     370                     375                          380

Phe  Ala  Asp  Gly  Gln  Pro  Lys  Leu  Val  Ser  Asp  Gln  Ala  Val  Ser  Leu
385                      390                          395                     400

Gly  Gln  Asn  Val  Leu  Ser  Ala  Asp  Phe  Thr  Pro  Gly  Thr  Glu  Tyr  Thr
               405                          410                          415

Val  Glu  Val  Arg  Phe  Lys  Glu  Phe  Gly  Ser  Val  Arg  Ala  Lys  Val  Val
               420                          425                     430

Ala  Gln  Lys  Arg  Gly  Val  Leu  Ser  Arg  Val  Ser
          435                      440
```

(2) INFORMATION FOR SEQ ID NO:3:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (xi) SEQUENCE DESCRIPTION: SEQ ID NO:3:

CATGGTTGAC AGCGAGG     17

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (xi) SEQUENCE DESCRIPTION: SEQ ID NO:4:

CCTCGCTGTC AACCATG     17

47-KILODALTON ANTIGEN OF *TREPONEMA PALLIDUM*

This application is a continuation-in-part of U.S. Ser. No. 07/658,630, filed Feb. 21, 1991, now abandoned, which is a continuation-in-part of U.S. Ser. No. 07/235,351, filed Aug. 23, 1988, now abandoned, which is a continuation of 06/913,724, filed Sep. 30, 1986, now U.S. Pat. No. 4,868,118, and a continuation-in-part of U.S. Ser. No. 07/940,245, filed Aug. 31, 1992, now U.S. Pat. No. 5,350,842, which is a continuation-in-part of 07/235,351, filed Aug. 23, 1988, now abandoned, which is a continuation of 06/913,724, filed Sep. 30, 1986, now U.S. Pat. No. 4,868,118.

The government may own certain rights in the present invention pursuant to Public Health Services grants AI-16692 and AI-17366.

BACKGROUND OF THE INVENTION

1. Field of the Invention

The present invention relates generally to compositions for use in the preparation of *Treponema pallidum* antigenic proteins and peptides. In particular aspects, the invention relates to recombinant DNA constructs for the preparation of selected *T. pallidum* antigenic/immunogenic proteins and peptides.

2. Description of the Related Art

*Treponema pallidum* and its various pathogenic subspecies comprise the etiologic agents of syphilis and other treponemal diseases. Despite the availability of effective antibiotics, syphilis continues to result in worldwide morbidity and mortality. One of the principal reasons behind the continued medical threat posed by syphilis is the fact that this disease can go undiagnosed, and can continue to be transmitted sexually. Moreover, by going undetected or undiagnosed, the disease can exert extensive damage, which may not be resolved by therapy. This can be a particular problem in the case of cardiovascular syphilis, neurosyphilis, and also a congenital form of the disease.

Both prevention and diagnosis are important aspects of an overall approach to treponemal disease control. Particularly in places where some treponemal diseases tend to be endemic, such as Central and South America, Asia, or Africa, preventative measures such as immunization against the disease would likely provide the most reasonable and successful long term approach. Immunization of individuals against the disease through the use of vaccines incorporating particular *T. pallidum* pathogen-specific immunogenic proteins(s) is an approach which could be attempted. Unfortunately, no such vaccine currently exists.

The physician, in an attempt to make an accurate diagnosis with no definitive historical, epidemiological, or clinical evidence of the disease, relies mostly upon serological results for accurate diagnosis. Unfortunately, the severe limitations and restrictions of the available serological procedures often preclude reliable diagnostic conclusions (83). It is well known that the immunologically non-specific non-treponemal screening tests for syphilis (VDRL, RPR circle card, ART) give false positive reactions not only among patients with acute and chronic diseases, but among pregnant women, vaccinees, and narcotic addicts (38, 39, 83, 84). Furthermore, false negative reactions occur commonly among patients with untreated latent and late syphilis (83, 40). Reliance, then, is placed upon the so-called "immunologically specific" confirmatory (treponemal) tests for syphilis (FTA-ABS, MHA-TP) to establish the presence or absence of the disease. Yet, these procedures also produce false positive reactions due to their technical and biological limitations, thereby creating the current diagnostic dilemma (83).

The lack of specificity of these tests stems from a two-fold problem. First, the preparation of either whole, killed *T. pallidum* (FTA-ABS test) or ultrasonic lysates of the organisms (MHA-TP test) requires organisms initially cultured in rabbit testes and thus necessitates the use of rabbit testis-contaminated *T. pallidum*. This contributes to false positive reactivity. Second, the presence of circulating cross-reactive antibody found in the serum of all humans (both patients and normal individuals) and elicited in response to the common antigens of host indigenous, non-pathogenic treponemas comprising the "normal bacterial flora" further complicates diagnostic accuracy. Although both the FTA-ABS and MHA-TP tests attempt to selectively bind these non-specific antibodies by the use of "sorbing" components prepared from one of the non-pathogenic treponemas (*T. phagedenas* biotype Reiter), their inability to effect a complete absorption of cross-reactive antibody results in false positive reactivities (83, 41–45). Additionally, the use of "sorbing" reagents contributes to the complexity of the procedures.

Within the past decade, groups of investigators have begun to characterize on a molecular level the structural components of the *Treponema pallidum*, subspecies pallidum (*T. pallidum*), bacterium in an attempt to provide useful tools for both diagnosis and the prevention of syphilis (1). Certain of these investigators have sought to identify and to analyze membrane proteins of the organism in an attempt to define important immunogens or potential virulence determinants (1,2). For example, monoclonal antibodies directed against a 47-kilodalton (kDa) antigen of *T. pallidum* were reported to possess treponemicidal activity in the *T. pallidum* immobilization test and in the in vitro-in vivo neutralization test of Bishop and Miller (3,4). Moreover, further work demonstrated that this antigen was abundant in *T. pallidum* and highly immunogenic in both human and experimental rabbit syphilis (4–6). Even further evidence indicated that the 47-kDa antigen had potential as a serodiagnostic antigen and that monoclonal antibodies directed against the 47-Kda antigen may be used for syphilis diagnosis (5,7–13).

The 47-kDa antigen is not localized to just one pathogenic subspecies in that other pathogenic subspecies of treponemas such as *T. pallidum* subsp. *pertenue*, *endemicum*, and *Treponema carateum* all apparently possess cognate 47-kDa antigens (4,10,14–17); for example, the predominant serologic response in patients with active pinta (*T. carateum*) was found to be directed against the 47-kDa antigen (18). Immunologic, physicochemical, and genetic data support the pathogen-specificity of the 47-kDa antigen (4,10–12,17, 19,20). Additional work on the 47-kDa antigen of *T. pallidum* by investigators other than the present inventor has recently been reviewed (11).

Up until the advent of the present invention, though, there has been no economical source for 47-kDa antigen. This is, of course, due to the requirement that *T. pallidum* can be grown only in connection with a living tissue, such as rabbit testicles. Moreover, in particular, there has been no recombinant DNA sources from which to prepare 47-kDa antigen proteins, peptides, or even specific DNA segments. Accordingly, an economic source for the provision of 47-kDa antigenic or immunogenic protein or peptides, a source free from possible contamination with animal or human viruses, would provide an important tool to be used in the diagnosis and/or possibly in the prevention of the disease.

SUMMARY OF THE INVENTION

Recognizing these and additional disadvantages in the prior art, it is a general object of the invention to provide improved methods and compositions useful in the preparation of the 47-kDa *T. pallidum* membrane antigen, antigenic/immunogenic subportions, or biologically functional equivalents thereof.

It is a further general object of the inventions to provide DNA compositions useful in the preparation of the 47-kDa *T. pallidum* antigen, or useful polypeptide variants thereof.

It is a more particular object of the invention to provide recombinant DNA molecules which encode immunogenic natural 47-kDa *T. pallidum* surface antigen, the DNA being capable of being expressed in a variety of hosts.

The invention thus represents a realization by the inventor that DNA encoding the 47-kDa membrane protein of *T. pallidum* may be successfully isolated, essentially free of associated cellular genes, and employed as a template in the preparation of antigenic as well as immunogenic polypeptides reactive with anti-47-kDa polyclonal and monoclonal antisera. As used herein, the term "47-kDa antigen" refers broadly to the 47-kDa *T. pallidum* membrane antigen, for example, as characterized in Ref.'s 11 and 23, as well as equivalent structures, such as those suggested by the present disclosure. Thus, in light of techniques known in the art and/or disclosed herein, the term is meant to include variants or analogs of the natural sequence protein, including allelic and functionally equivalent variations, deacylated analogs and antigenic/immunogenic peptidyl subfragments of any of these.

In certain embodiments, the invention is thus concerned with the preparation of the natural 47-kDa sequence, such as defined by amino acid sequences disclosed in SEQ ID NO: 2 of the present disclosure, whether naturally derived from recombinant sources, or biological functional equivalents thereof.

In general, as used herein, the phrase "biologically functional equivalent" amino acids refers to the fact that the invention contemplates that changes may be made in certain of the foregoing amino acid sequence(s) (e.g., by natural genetic drift, strain or subspecies antigenic variation, or by mutation of the DNA molecules hereof), without necessarily reducing or losing their antigenic/immunogenic identity. For example, the sequence can be altered through considerations based on similarity in charge (e.g., acidity or basic charges of the amino acid side group), hydrophatic index, or amphipathic score. In general, these broader aspects of the invention are founded in part on the general understanding in the art that certain amino acids may be substituted for other like amino acids without appreciable loss of the peptide's ability to bind to the antibodies, and thus be recognized antigenically, or alternatively, interact with antibody forming cells to elicit an immune response. Exemplary amino acid substitutions are set forth hereinbelow.

Accordingly, the present invention provides a nucleic acid molecule having a sequence may be further defined as comprising the amino acid sequence of SEQ ID NO: 2.

Particular embodiments of the invention include nucleic acid molecules encoding an amino acid sequence comprising the sequence extending from the amino acid Val at position 1 through the amino acid Gln at position 434, or through Set at position 444, representing the full natural sequence of the two most likely expressed 47-kDa antigens.

However, in even more particular embodiments, the invention comprises nucleic acid molecules encoding various peptide sequences shown in SEQ ID NO:2, for example, the peptide sequence extending from about the amino acid Cys at position 20 through the Tyr at position 29, the amino acid Val at position 92 through the amino acid Ser at position 119; the sequence extending from amino acid Asp at position 132 through the amino acid Glu at position 145; the sequence extending from the amino acid Met at position 158 through the amino acid Asn at position 168; the sequence extending from the amino acid Val at position 181 through the amino acid Asn at position 206; the sequence extending from the amino acid Arg at position 243 through the amino acid Phe at position 267; as well as nucleic acid sequences encoding biologically functional equivalents of the foregoing peptides. These peptidyl regions have been selected in that it has been discovered by the present inventor that they comprise generally hydrophilic peptidyl regions, and are thus generally preferred for use as immunogenic/antigenic peptides in the practice of aspects of the invention. In still another embodiment, the nucleic acid molecule of the invention encodes an analog of the 47-kDa antigen from which the Cys-20 residue is absent.

In certain other aspects, the invention concerns nucleic acid molecules comprising sequences corresponding to the natural 47-kDa antigen gene, or selected subportions thereof, which sequences it is contemplated will have significant utility irrespective of whether they encode antigenic peptides. In such aspects, it is contemplated, for example, that shorter or larger nucleic acid fragments of the 47-kDa antigen gene, prepared synthetically or otherwise, can be employed as hybridization probes. Such probes can readily be employed in a variety of manners, including their use in the detection of pathogenic *T. pallidum* in selected biological or clinical samples, such as, but not limited to, lesion exudate, cerebrospinal fluid, biopsy specimens or amniotic fluid. By way of useful applications, as well as DNA hybridization techniques, one may wish to refer to references such as Ref. 78, U.S. Pat. No. 4,358,535, or U.S. Ser. No. 129,255 filed Dec. 7, 1987, incorporated herein by reference.

In such embodiments, the nucleic acid molecule selected, whether DNA or RNA, will generally include at least a 10 or 20 nucleotide segment of the 47-kDa antigen nucleic acid sequence of SEQ ID NO: 1, with the nucleic acid molecule as a whole being capable of forming a detectable stable duplex with said sequence under standard selective nucleic acid hybridization conditions (78–80). The 10 or 20 base pair size is selected as a general lower limit in that at sizes smaller than 10 bases, hybridization stabilization during washing steps following hybridization can become a problem, resulting in much lower signal/noise ratios. Moreover, as the size of the probe decreases to much below 7 to 8 or 10 bases, nonspecific hybridization may occur to genes having complementary sequences over short stretches.

In more preferred embodiments, the invention contemplates the preparation and use of nucleic acid molecules whose structure includes sequences comprising at least an about 17 or 20 nucleotide segment of the nucleic acid sequence of SEQ ID NO: 1, said nucleic acid molecule being capable of hybridizing to the nucleic acid sequence of SEQ ID N0: 1, or the recombinant insert of pMN23, under hybridization stringency conditions standard for hybridization fidelity and stability. These embodiments recognize that hybridization probes larger than a lower limit of about 10 or about 20 bases provide more specific stable and overall more dependable hybridization. The only disadvantage to the longer probes is that the expense of preparation can increase somewhat where the fragment is prepared synthetically. However, with the advent of DNA synthesizing machines and PCR technology (U.S. Pat. No. 4,683,202, incorporated herein by reference), the expense of preparing larger DNA or RNA probes can be obviated.

Most preferably, the present invention provides a DNA segment having a sequence encoding a 47-kDa surface immunogen of *Treponema pallidum*, said sequence being substantially free of *Treponema pallidum* sequences not encoding the 47-kDa *Treponema pallidum* antigen.

In certain additional embodiments, the invention concerns the preparation of recombinant vectors which incorporate one or more of the foregoing DNA molecules, which vectors may be employed either in the preparation of nucleic acid sequences, or for expression of the DNA to produce 47-kDa antigen sequences. Thus, as used herein, the term "recombinant vector" refers to chimeric DNA molecules which include vector DNA capable of replicating in selected host organisms, whether prokaryotic hosts such as *E. coli* or *Bacillus subtilis*, or higher organisms such as yeast, CHO or African green monkey cells.

In further aspects, the present disclosure relates to the 47-kDa antigen itself, as well as antigenic/immunogenic subfragments thereof comprising polypeptides of between about 10 and about 30 amino acids in length, characterized by an ability to cross react immunologically with antisera reactive against the 47-kDa *T. pallidum* membrane antigen. Most particularly, these antigens may be described as hydrophobic antigens, characterized by an ability to not cross-react immunologically with antisera reactive against more hydrophilic forms of *T. pallidum* antigen.

As used herein, the phrase "having an ability to cross react immunologically with antisera specific for the 47-kDa antigen", refers generally to the ability to cross-react immunologically with polyclonal antisera of humans, rabbits, or other animals, such as described in Refs. 4, 10–12, 17, 19, 23, 55, or monoclonal antibodies, as described in U.S. Pat. Nos. 4,514,498 and 4,740,407, the foregoing references being incorporated herein by reference.

Thus, in preferred aspects, the invention concerns antigenic/immunogenic 47-kDa peptide sequences, either naturally derived from *T. pallidum* or recombinant *E. coli*, or synthetically prepared "synthetic peptides" of SEQ ID NO: 2, corresponding to the individual peptides extending from about the amino acid Cys at position 20 through the Tyr at position 29, the amino acid Val at position 92 through the amino acid Ser at position 119; the peptide sequence extending from amino acid Asp at position 132 through the amino acid Glu at position 145; the peptide sequence extending from the amino acid Met at position 158 through the amino acid Ash at position 168; the peptide sequence extending from the amino acid Val at position 181 through the amino acid Asn at position 206; the peptide sequence extending from the amino acid Arg at position 243 through the amino acid Phe at position 267; as well as biologically functional equivalents of the foregoing peptides. It is contemplated that such peptides will find utility both as antigens, for example, in immunologic detection assays, or as immunogens in the formation of vaccines.

For greatest utility in the case of vaccine or antigen formulations, one will desire to employ peptides having a length ranging from about 10, 11, or 19, to about 30 amino acids in length, with about 11, 14, 25, 26, or 28 being preferred.

For the preparation of vaccine formulations suitable for parenteral administration, the immunogens of the invention may be formulated in sesame or peanut oil, aqueous propylene glycol, in liposomes or Iscoms (81,82) or in sterile aqueous solutions. Such solutions are typically suitably buffered if necessary and the liquid diluent first rendered isotonic with sufficient saline or glucose. Additionally, stabilizers in the form of, for example, sorbitol or stabilized gelatin may be included. These particular aqueous solutions are particularly well suited for intramuscular and subcutaneous injection, as is generally preferred for vaccination using antigenic preparations.

However, to increase the potential immunogenicity, and thereby improve the performance of antigen-containing pharmaceutical preparations, one may additionally desire to include various immunoadjuvants, such as the water-in-oil emulsion developed by Freund. The basic ingredients of light mineral oil (Bayol) and emulsifying agent mixtures such as Arlacel (A or C) are available commercially. The antigens are emulsified in either solutions or suspensions of the immunogen (incomplete Freund's adjuvant). Moreover, the addition of parts or whole killed mycobacteria (*M. butyricum, M. tuberculosis*) in small amounts to the suspension (complete Freund's adjuvant) leads to a further enhancement of the immunogenicity of the pharmaceutical vaccines made in accordance with the present invention. Recent adjuvants composed of monophosphoryl lipid A (46, 47) also may be applicable.

In still further aspects, the invention concerns highly purified preparations of the full length 47-kDa antigen itself, said antigen not being heretofore available in a substantially purified form. In preferred aspects, the invention concerns the 47-kDa antigen, derived from recombinant sources.

In still further aspects, it is pointed out that the structure of the 47-kDa antigen is such that it is subjected to various modifications by the *T. pallidum* cell following translation. For example, the 47-kDa precursor is apparently translated with a short leader sequence that is removed during translation and insertion of the protein into the *T. pallidum* membrane, leaving a diacylglycerol modified cysteine residue at position 20 (Cys-20) as the N-terminal amino acid. This cysteine residue is, in turn, subjected to further modification by the cell, including the attachment of an amide-linked fatty acid.

While it is believed by the inventor that this acylation may serve an important biological role, it is also believed to result in certain disadvantages at times, in that it tends to make isolation of the protein more difficult. Therefore, in certain aspects, the invention is directed to deacylated analogs of the 47-kDa protein (and underlying gene) which have been modified to remove either the acylation consensus sequence or the Cys residue, such as through removal of the Cys codon from the gene by genetic engineering, or alteration of the acylation recognition sequence.

DETAILED DESCRIPTION OF THE PREFERRED EMBODIMENTS

Figure 1:
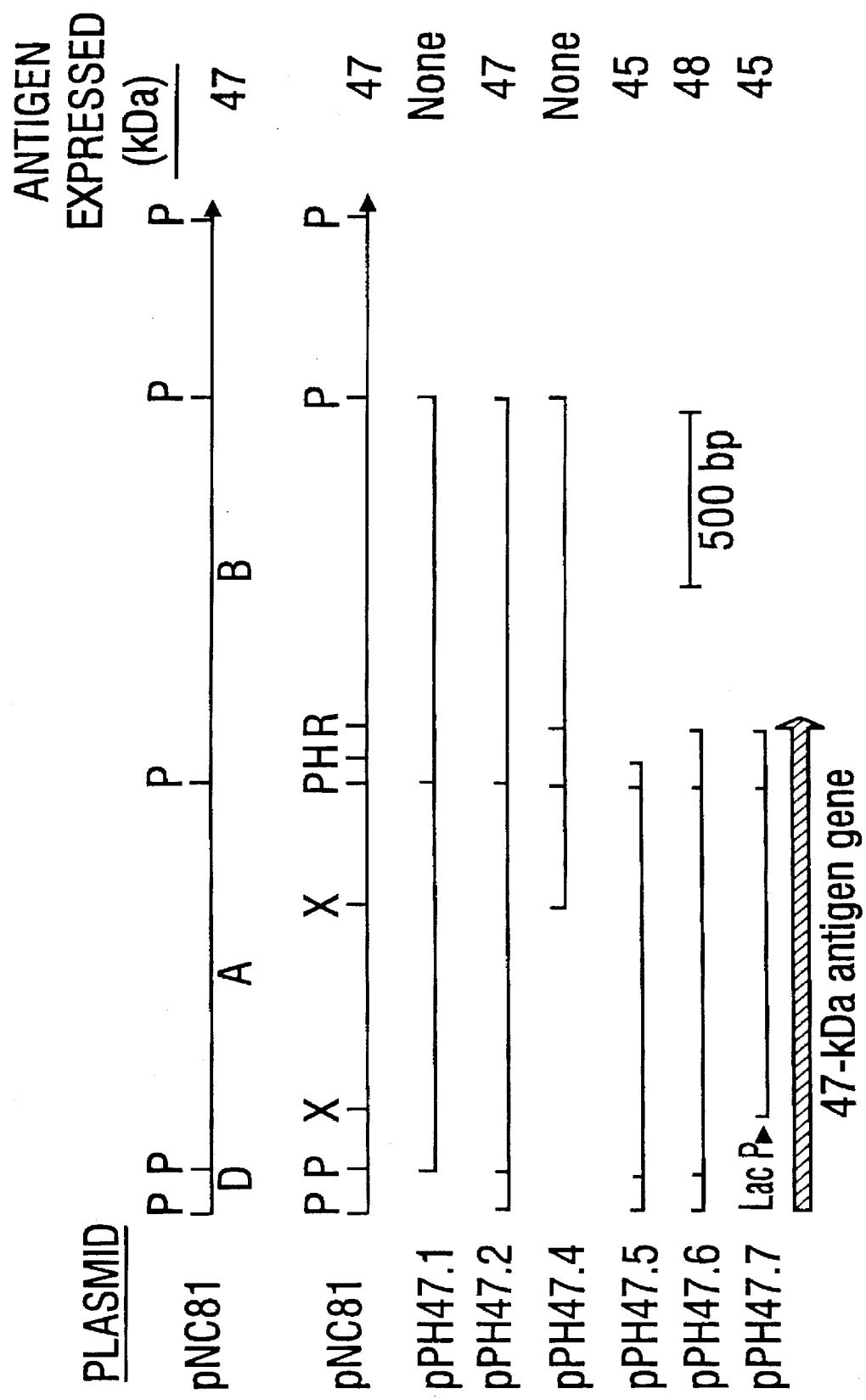
FIG. 1. Partial restriction enzyme maps and relevant expression products of 47-kDa antigen-encoding plasmid derivatives. Plasmid pNC81 (top) has indicated PstI fragments A, B, and D which collectively comprise a 2.4 kb DNA fragment containing the 47-kDa antigen encoding region. Restriction sites for pNC81 (bottom) are designated as P (PstI), X (XhoII), K (KpnI), H (HindIII), and R (EcoRI). The extent of the 47-kDa antigen gene sequence in each subclone is represented by the solid line. The cloning vector for all pPH subclones was pUC19. With the exception of pPH47.7, transcription of the 47-kDa antigen gens was opposite to that of the direction of the lac promoter.

This invention concerns a variety of embodiments which relate to the preparation and use of the 47-kDa antigen of T. pallidum. For example, the invention discloses for the first time the preparation of the 47-kDa antigen in a purified state, in significant quantities, and from either natural or recombinant DNA sources. Moreover, the information provided by the present invention allows the recombinant preparation of mutant or variant protein species, through the application of techniques such as DNA mutagenesis. Accordingly, included in the present disclosure is information which allows the preparation of a wide variety of DNA fragments having a number of potential utilities—ranging from DNA sequences encoding relatively short immunogenic/antigenic peptidyl subfragments of the 47-kDa antigen, to DNA or RNA sequences useful as hybridization probes for in vitro diagnosis, research, as well as other useful medical and biomedical applications.

In the inventor's copending application Ser. No. 913,724 is described the cloning and expression of the natural 47-kDa antigen DNA sequence as it is isolated from T. pallidum cells. Particular embodiments described therein relate to the preparation of recombinant vectors including DNA inserts encoding the natural 47-kDa antigen gene and expressing that DNA in microbial clones to produce the 47-kDa antigen. While this copending application broadly enables the preparation and use of DNA sequences, in general, which encode the antigen, an exemplary plasmid, designated pMN23, has been deposited with the ATCC in host E. coli cells (accession number 67,204), in order to provide a ready and accessible source of exemplary, recombinant 47-kDa antigen and DNA to the art.

Nucleic Acid Hybridization Embodiments

As mentioned, in certain aspects, the DNA sequence information provided by the invention allows for the preparation of relatively short DNA (or RNA) sequences having the ability to specifically hybridize to gene sequences of the 47-kDa antigen gene. In these aspects, nucleic acid probes of an appropriate length are prepared based on a consideration of the natural sequence shown in SEQ ID NO:1, or derived from flanking regions of the 47-kDa gene, such as regions downstream of the gene as found in plasmid pMN23. The ability of such nucleic acid probes to specifically hybridize to the 47-kDa gene sequences lend them particular utility in a variety of embodiments. Most importantly, the probes can be used in a variety of diagnostic assays for detecting the presence of pathogenic organisms in a given sample. However, either uses are envisioned, including the use of the sequence information for the preparation of mutant species primers, or primers for use in preparing other genetic constructions.

To provide certain of the advantages in accordance with the invention, the preferred nucleic acid sequence employed for hybridization studies or assays includes sequences that are complementary to at least a 10 to 20, or so, nucleotide stretch of the sequence shown in SEQ ID NO:1. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. Thus, one will generally prefer to design nucleic acid molecules having 47-kDa gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, or by introducing selected sequences into recombinant vectors for recombinant production.

In that the 47-kDa antigen is indicative of pathogenic Treponema species, the present invention will find particular utility as the basis for diagnostic hybridization assays for detecting 47-kDa-specific RNA or DNA in clinical samples. Exemplary clinical samples that can be used in the diagnosis of infections are thus any samples which could possibly include treponemal nucleic acid, including skin lesions, lesion exudates, amniotic fluid or other body fluids or the like. A variety of hybridization techniques and systems are known which can be used in connection with the hybridization aspects of the invention, including diagnostic assays such as those described in Falkow et al., U.S. Pat. No. 4,358,535 and Norgard, copending U.S. Ser. No. 129,255.

Accordingly, the nucleotide sequences of the invention are important for their ability to selectively form duplex molecules with complementary stretches of the 47-kDa gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and/or high temperature conditions, such as provided by 0.02M–0.15M NaCl at temperatures of 50° to 70° C. These conditions are particularly selective, and tolerate little, if any, mismatch between the probe and the template or target strand.

Of course, for some applications, for example, where one desires to prepare mutants employing a mutant primer strand hybridized to an underlying template, less stringent hybridization conditions are called for in order to allow formation of the heteroduplex. In these circumstances, one would desire to employ conditions such as 0.15M–0.9M salt, at temperatures ranging from 20° to 55° C. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In clinical diagnostic embodiments, nucleic acid sequences of the present invention are used in combination with an appropriate means, such as a label, for determining hybridization. A wide variety of appropriate indicator means are known in the art, including radioactive, enzymatic or other ligands, such as avidin/biotin, which are capable of giving a detectable signal. In preferred diagnostic embodiments, one will likely desire to employ an enzyme tag such as fluorescence, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with pathogen nucleic acid-containing samples.

In general, it is envisioned that the hybridization probes described herein will be useful both as reagents in solution hybridization as well as in embodiments employing a solid phase. In embodiments involving a solid phase, the test DNA (or RNA) from suspected clinical samples, such as exudates, body fluids (e.g., amniotic fluid cerebrospinal fluid) or even tissues, is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Purified 47-kDa Antigen

The present invention further provides various means for both producing and isolating the 47-kDa antigen protein, ranging from isolation of essentially pure protein from natural sources (e.g., from *T. pallidum* bacterial cells), or its isolation from recombinant DNA sources (e.g. *E. coli* or microbial cells). Additionally, by application of techniques such as DNA mutagenesis, the present invention allows the ready preparation of so-called "second generation" or analog molecules having modified or simplified protein structures, or even analogs which have been engineered to remove acylation sites (i.e., deacylated analogs). Second generation proteins will typically share one or more properties in common with the full-length antigen, such as a particular antigenic/immunogenic epitopic core sequence. Epitopic sequences can be provided on relatively short molecules prepared from knowledge of the peptide, or underlying DNA sequence information, provided by the present invention. Such variant molecules may not only be derived from selected immunogenic/antigenic regions of the protein structure, but may additionally, or alternatively, include one or more functionally equivalent amino acids selected on the basis of similarities or even differences with respect to the natural sequence.

Isolation of the 47-kDa antigen from either natural or recombinant sources in accordance with the invention is achieved preferably by detergent extraction of the protein from recombinant or *T. pallidum* cells with an ionic or non-ionic detergent, such as Sarkosyl or Triton X-114, in order to first solubilize the antigen. The detergent solution containing the solubilized antigen is then centrifuged or otherwise filtered to remove insoluble material, and passed over an immunoaffinity column. Other important considerations include the significant hydrophobic nature of the protein, not readily apparent from its primary amino acid sequence, that causes it to complex or aggregate with other hydrophobic moieties, making purification of the protein problematic. In this regard, chromatofocusing can be used as an additional purification aid. A preferred immunoadsorbent antibody is provided by monoclonal antibody 11E3 (ATCC HB9781) or 8G2 (ATCC HB8134). However, in general, useful antibodies may be prepared as described in earlier patents (see, e.g., U.S. Pat. Nos. 4,514,498 and 4,740,467), and those reactive with the desired protein or peptides selected. When detergent solubilized and immunoabsorbed as disclosed herein, it is found that the 47-kDa antigen may be obtained in a highly purified state, appearing as essentially a single band upon polyacrylamide gel analysis. Moreover, it is believed that the foregoing isolation scheme will work equally well for isolation of antigenic/immunogenic subfragments of the protein, requiring only the generation and use of antibodies having affinity for the desired peptidyl region.

Particular embodiments disclosed herein are directed to the production of 47-kDa antigen by recombinant DNA cells in greatly improved quantities than previously available. For example, it has been discovered that placement of the antigen gene under the control of a T7 RNA polymerase expression system improves the expression of the 47-kDa antigen over earlier constructs by 20-fold in certain hosts (e.g., *E. coli* K38), and even 100-fold in others (e.g., *E. coli* RR1). Thus it appears to be the case that the 47-kDa gene is amenable to transcriptional enhancement, and can be juxtaposed to heterologous promoters to achieve a greatly improved production of protein. A variety of possible promoters arrangements are disclosed in some detail below, as well as a specific description of the preferred T7 promoter arrangement.

Epitopic Core Sequences of the 47-kDa Antigen

As noted above, particular advantages of the invention may be realized through the preparation of synthetic peptides which include epitopic/immunogenic core sequences. These epitopic core sequences are identified herein in particular aspects as hydrophilic regions of the 47-kDa antigen. It is proposed that these regions represent those which are most likely to promote T-cell or B-cell stimulation, and, hence, elicit specific antibody production. An epitopic core sequence, as used herein, is a relatively short stretch of amino acids that is "complementary" to, and therefore will bind, antigen binding sites on anti-47-kDa antibodies. It will be understood that in the context of the present disclosure, the term "complementary" refers to amino acids or peptides that exhibit an attractive force towards each other. Thus, epitope core sequences of the present invention may be operationally defined in terms of their ability to compete with or even displace the binding of the 47-kDa antigen with anti-47-kDa antisera.

In general, the size of the polypeptide antigen is not believed to be particularly crucial, so long as it is at least large enough to carry the identified core sequence or sequences. The smallest core sequence of the present disclosure is on the order of about 11 amino acids in length. Thus, this size will generally correspond to the smallest peptide antigens prepared in accordance with the invention. However, the size of the particular core sequences identified by the invention ranges from 11 to 28 amino acids in length. Thus, the size of the antigen may be larger where desired, so long as it contains the basic epitopic core sequence.

Accordingly, the inventor has identified particular peptidyl regions of the 47-kDa antigen which are believed to constitute epitopic core sequences comprising particular epitopes of the protein. These epitopic core sequences are illustrated by reference to SEQ ID NO:2 as corresponding to the putative N-terminus of the mature molecule (amino acids 20–29) and individual peptides extending from about the amino acid Val at position 92 through the amino acid Ser at position 119; the peptide sequence extending from amino acid Asp at position 132 through the amino acid Glu at position 145; the peptide sequence extending from the amino acid Met at position 158 through the amino acid Asn at position 168; the peptide sequence extending from the amino acid Val at position 181 through the amino acid Asn at position 206; the peptide sequence extending from the Amino acid Arg at position 243 through the amino acid Phe at opposition 267; as well as biologically functional equivalents of the foregoing peptides, as explained in more detail below.

Syntheses of the foregoing sequences, or peptides which include the foregoing within their sequence, is readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of the peptides of the invention, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of 7.0 to 7.5. Moreover, it may be desirable to include agents which will inhibit microbial growth, such as sodium azide or Merthiolate™. For extended storage in an aqueous state it will be desirable to store the solutions at 4° C., or more preferably, frozen. Of course, where the peptide(s) are stored in a lyophilized or powdered state, they may be stored virtually indefinitely, e.g., in metered aliquots that may be rehydrated with a predetermined amount of water (preferably distilled) or buffer prior to use.

Biological Functional Equivalent Amino Acids

As noted above, it is believed that numerous modification and changes may be made in the structure of the 47-kDa antigen, or antigenic/immunogenic subportions thereof, and still obtain a molecule having like or otherwise desirable characteristics.

For example, certain amino acids may be substituted for other amino acids in a protein structure without appreciable loss of interactive binding capacity with complementary structures such as antigen-binding regions of antibodies (or, e.g., binding sites on receptor molecules). It is thus hypothesized by the present inventor that various changes may be made in the sequence of the antigenic peptides without appreciable loss of their antibody-binding, or 47-kDa antigen competing, activity. If the molecule contains covalently-linked fatty acids, as is implicit in its DNA sequence and corresponding amino acid sequence of Val-17 through Cys-20, SEQ ID NO:2, site-directed mutagenesis can be used to eliminate fatty acylation sites.

The importance of the hydropathic index of amino acids in conferring interactive biologic function on a protein has been discussed generally by Kyte et al. (37), wherein it is found that certain amino acids may be substituted for other amino acids having a similar hydropathic index or core and still retain a similar biological activity. As displayed in the table below, amino acids are assigned a hydropathic index on the basis of their hydrophobicity and charge characteristics. It is believed that the relative hydropathic character of the amino acid determines the secondary structure of the resultant protein, which in turn defines the interaction of the protein with substrate molecules.

TABLE I

| Amino Acid | Hydropathic Index |
|---|---|
| Isoleucine | 4.5 |
| Valine | 4.2 |
| Leucine | 3.8 |
| Phenylalanine | 2.8 |
| Cysteine/cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

Thus, for example, isoleucine, which has a hydropathic index of +4.5, can be substituted for valine (+4.2) or leucine (+3.8), and still obtain a protein having similar biologic activity. Alternatively, at the other end of the scale, lysine (−3.9) can be substituted for arginine (−4.5), and so on.

Accordingly, these amino acid substitutions are generally based on the relative similarity of R-group substituents, for example, in terms of size, electrophilic character, charge, and the like. In general, preferred substitutions which take various of the foregoing characteristics into consideration include the following:

TABLE II

| Original Residue | Exemplary Substitutions |
|---|---|
| Ala | gly; ser |
| Arg | lys |
| Asn | gln; his |
| Asp | glu |
| Cys | ser |
| Gln | asn |
| Glu | asp |
| Gly | ala |
| His | asn; gln |
| Ile | leu; val |
| Leu | ile; val |
| Lys | arg; gln; glu |
| Met | met; leu; tyr |
| Ser | thr |
| Thr | ser |
| Trp | tyr |
| Tyr | trp; phe |
| Val | ile; leu |

Immunoassays

It is proposed that the 47-kDa antigen's peptides or analogs of the invention will find utility as immunogens in connection with vaccine development, or as antigens in immunoassays for the detection of anti-47-kDa antigen-reactive antibodies. Turning first to immunoassays, in their most simple and direct sense, preferred immunoassays of the invention include the various types of enzyme linked immunosorbent assays (ELISAs) known to the art. However, it will be readily appreciated that utility is not limited to such assays, and useful embodiments include RIAs and other non-enzyme linked antibody binding assays or procedures.

In the preferred ELISA assay, peptides incorporating the 47-kDa antigen sequences are immobilized onto a selected surface, preferably a surface exhibiting a protein affinity such as the wells of a polystyrene microtiter plate. After washing to remove incompletely adsorbed material, one will desire to bind or coat a nonspecific protein such as bovine serum albumin (BSA) or casein onto the well that is known to be antigenically neutral with regard to the test antisera. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween. These added agents also tend to assist in the reduction of nonspecific background. The layered antisera is then allowed to incubate for from 2 to 4 hours, at temperatures preferably on the order of 25° to 27° C. Following incubation, the antisera-contacted surface is washed so as to remove non-immunocomplexed material. A preferred washing procedure includes washing with a solution such as PBS/Tween, or borate buffer.

Following formation of specific immunocomplexes between the test sample and the bound antigen, and subsequent washing, the occurrence and even amount of immunocomplex formation may be determined by subjecting same to a second antibody having specificity for the first. Of course, in that the test sample will typically be of human origin, the second antibody will preferably be an antibody having specificity in general for human Ig. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS-Tween).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

Vaccine Preparation and Use

Immunogenic compositions, believed to be suitable for use as an anti-treponemal vaccine or natural adjuvant(s), may be prepared most readily directly from immunogenic 47-kDa proteins and/or peptide analogs prepared and purified in a manner disclosed herein. Preferably the purified material is also extensively dialyzed to remove undesired small molecular weight molecules and/or lyophilization of the thus purified material for more ready formulation into a desired vehicle.

The preparation of vaccines which contain peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of 0.5% to 10%, preferably 1–2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain 10–95% of active ingredient, preferably 25–70%.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescent labeling agents, and the like. These techniques are well known and may be found in a wide variety of patents, such as U.S. Pat. Nos. 3,791,932; 4,174,384 and 3,949,064, as illustrative of these types of assays.

Site-Specific Mutagenesis

As noted above, site-specific mutagenesis is a technique useful in the preparation of individual peptides, or biologically functional equivalent or analog proteins or peptides, derived from the 47-kDa antigen sequence, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications such as reference 59, incorporated herein by reference. As will be appreciated, the technique typically employs a phage vector which exists in both a single stranded and double stranded form. Typical vectors useful in site-directed mutagenesis include vectors such as the M13 phage, for example, as disclosed by reference 60, incorporated hereby in reference. These phage are readily commercially available and their use is generally well known to those skilled in the art.

In general, site-directed mutagenesis in accordance herewith is performed by first obtaining a single-stranded vector which includes within its sequence a DNA sequence which encodes the 47-kDa antigen. An oligonucleotide primer bearing the desired mutated sequence is prepared, generally synthetically, for example by the method of reference 61. This primer is then annealed with the singled-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells and clones are selected which include recombinant vectors bearing the mutated sequence arrangement.

Host Cell Cultures and Vectors

In general, of course, prokaryotes are preferred for the initial cloning of DNA sequences and constructing the vectors useful in the invention. For example, E. coli. K12 strain 294 (ATCC No. 31446) is particularly useful. Other microbial strains which may be used include E. coli strains such as E. coli B, and E. coli X 1776 (ATCC No. 31537). These examples are, of course, intended to be illustrative rather than limiting.

Prokaryotes may also be used for expression. The aforementioned strains, as well as E. coli W3110 (F-, lambda-, prototrophic, ATCC No. 273325), bacilli such as Bacillus subtilis, or other enterobacteriaceae such as Salmonella typhimurium or Serratia marcescens, and various Pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR 322, a plasmid derived from an E. coli species (see, e.g., ref. 62). pBR 322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

Those promoters most commonly used in recombinant DNA construction include the B-lactamase (penicillinase) and lactose promoter systems (63,64,65) and a tryptophan (trp) promoter system (66,67). While these are the most commonly used, other microbial promoters have been discovered and utilized, and details concerning their nucleotide sequences have been published, enabling a skilled worker to ligate them functionally with plasmid vectors (67).

In addition to prokaryotes, eukaryotic microbes, such as yeast cultures may also be used. Saccharomyces cerevisiae, or common baker's yeast is the most commonly used among eukaryotic microorganisms, although a number of other strains are commonly available. For expression in Saccharomyces, the plasmid YRp7, for example, is commonly used (69,70,71). This plasmid already contains the trpl gene which provides a selection marker for a mutant strain of yeast lacking the ability to grow in tryptophan, for example ATCC No. 44076 or PEP4-1 (72). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (73) or other glycolytic enzymes (74,75), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (76). Examples of such useful host cell lines are VERO and HeLa cells, Chinese hamster ovary (CHO) cell lines, and W138, BHK, COS-7 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

For use in mammalian cells, the control functions on the expression vectors are often provided by vital material. For example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 vital origin of replication (77). Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

As origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

EXAMPLE I

Nucleotide and corresponding Amino Acid, Sequence of the 47-kDa Antigen Gene

The present Example illustrates steps employed by the inventor in reducing certain aspects of the invention to practice. In particular, the Example relates to the structural analysis and sequencing of the cloned 47-kDa antigen gene. The general steps which may be employed in isolating such a gene are disclosed in the inventor's copending Ser. No. 06/913,724, filed Sep. 30, 1986. The present Example discloses the use of one of the more preferred clones isolated by the foregoing procedures, designated plasmid pMN23, in the sequencing of the 47-kDa antigen gene. (Deposited with the ATCC in *E. coli* and expressing the 47K *T. pallidum* antigen, ATCC designation 67204).

In addition to DNA sequencing studies, N-terminal amino acid sequencing of selected trypsin and hydroxylamine cleavage fragments of the native 47-kDa antigen was employed to assist in establishing the correct reading frame of the DNA and confirming the DNA sequence. In this regard, 33% of the entire (mature, without leader peptide) 47-kDa antigen amino acid content was sequenced and found to have 100% correlation with the predicted amino acid sequence derived from DNA sequencing of the cloned gene. This is the first major treponemal antigen sequenced where DNA sequencing data has been corroborated by determination of the amino acid sequence for a substantial proportion of the purified native (*T. pallidum*) protein.

MATERIALS AND METHODS

Bacterial strains. The virulent Nichols strain of *T. pallidum* subsp. pallidum was used as the representative pathogen in this study. It was maintained and cultivated in the testicles of New Zealand White rabbits without the use of cortisone acetate injections as described (19,55). Ten days after inoculation, rabbits were sacrificed by intravenous injection of T-61 Euthanasia solution (American Hoescht Corp., Somerville, N.J.), and the testes were aseptically removed. Treponemes were extracted on a rotary shaker in phosphate-buffered saline (PBS) (pH 7.4), and were isolated by differential centrifugation (55). Treponemes were suspended in PBS for final darkfield microscopic enumeration prior to use in antigen extraction. *E. coli* DH5 alpha (F$^-$ endA1 hsdR17 [$r_k^-m_k^+$] super4 thi-1 lambda$^-$ recA1 gyrA relA1 ø80dlac Zdelta M15 delta [lacZYA-argF] U169) (Bethesda Research Laboratory, Gaithersburg, Md.) was used as the recipient for pUC series plasmid derivatives (21). *E. coli* JM101 ([$r_k^+m_k^+$] delta [lac pro AB] thi supE/F' traD36 proA+proB+lacI$^Q$ lac Zdelta M15) (22) was used to harbor M13 derivatives for DNA sequencing analyses.

Plasmids and subcloning into pUC19. Plasmid derivatives were constructed as subclones of pNC81 (23), which originated from plasmid pMN23 (11). Plasmid pPH47.1 (containing PstI fragments A and B) (23) and pPH47.2 (possessing PstI fragments A, B, and D) (23) were generated by inserting the 2.3 kilobase (kb) and 2.36 kb partial PstI fragments of pNC81 (23) into pUC19 vector (21). Plasmid pPH47.5 was generated by digesting pPH47.2 with KpnI and recircularization (23). Plasmid pPH47.5 was generated by digesting pPH47.2 with HindIII and recircularization. Plasmid pPH47.6 was constructed by inserting the 1.35 kb EcoRI fragment of pPH47.2 into pUC19. Plasmid pPH47.7 was made by inserting the 1.1 kb XhoII-EcoRI fragment of pPH47.2 into the BamHI-EcoRI sites of pUC19. In this construction, transcription of the 47-kDa antigen mRNA is initiated from the lac promoter of pUC19. With the exception of pPH47.4, transcription of 47-kDa antigen mRNA was opposite to the direction of the lac promoter in the pUC plasmids. The 47-kDa protein derivatives expressed by pPH47.5, pPH47.6, and pPH47.7 are truncated but contain varying numbers of amino acids (i.e., approximately 29, 46, and 8 amino acids, respectively) encoded by the plasmid vector sequence(s). Expression of 47-kDa antigen derivatives by the various plasmids was assessed by immunoblotting expression products with monoclonal antibody 11E3 (4) and rabbit anti-*T. pallidum* antiserum (4,23).

Isolation of native 47-kDa antigen from *T. pallidum* by Triton X-114 phase partitioning. Triton X-114 extraction and phase separation of the 47-kDa *T. pallidum* protein was performed as described by Bordier (24) and as modified by Radolf et al. (54). Briefly, whole *T. pallidum* ($1\times10^{11}$) collected by differential centrifugation were extracted by rocking in a test tube end-over-end overnight with 40 ml of PBS containing 2% (v/v) Triton X-114 at 4° C. The insoluble material was removed by centrifugation at 27,000×g (4° C.) for 20 min. The supernatant containing soluble material was decanted and allowed to cloud in a 37° C. waterbath for 1 min, followed by centrifugation at 13,000×g (20° C.) for 2 min. The aqueous phase was removed and discarded.

At this stage, the material was processed in either of two ways: 1) the detergent phase (8 ml) was washed five times by repeated dilution to 28 ml with ice-cold PBS followed by mixing, rewarming, and centrifugation at 13,000×g (20° C.) for 2 min. The proteins in the washed detergent phase were then precipitated overnight at –20° C. with a 10-fold volume of cold acetone; 2) alternatively, for affinity purification prior to hydroxylamine cleavage, the Triton X-114 extract was washed three times in 1 ml of 10 mM Tris-HCl (pH 8.0)+5 mM NaCl. The washed detergent phase was diluted to 1% Triton X-114 in the 10 mM Tris-HCl (pH 8.0)+5 mM NaCl buffer. One ml of ReactiGel 6X (Pierce Chemical Co., Rockford, Ill.) containing 2 mg of monoclonal antibody 11E3 (ATCC Deposit HB9781) per ml of resin was added batchwise to the diluted detergent phase (23). This was incubated with end-over-end motion overnight at 4° C. The resin was then poured into a column and was washed with 5 bed volumes of 10 mM Tris-HCl (pH 8.0)+5 mM NaCl+ 1% Triton X-114. Purified 47-kDa antigen was eluted with 5 bed volumes of 3M guanidine-HCl (pH 5.5) +1% Triton X-114 (flow rate of 1 drop per 8 sec).

Hydroxylamine cleavage of the native 47-kDa antigen. Purified 47-kDa anti9en was dialyzed overnight against 18 L of distilled H$_2$O to remove guanidine-HCl. The protein was precipitated overnight with 10 volume of cold acetone (–20° C.). Precipitated protein was collected by centrifugation at 13,000×g for 10 min. The pellet was suspended in 6 M guanidine-HCl+2M hydroxylamine (HA) (pH 9.0) (25), and was incubated at 45° C. for 4 hr. The reaction mixture (1 ml) was dialyzed against 1 L of distilled H$_2$O overnight (4° C.) using 1,000 molecular weight exclusion dialysis tubing. The protein was lyophilized and about 100 pmoles of HA-cleaved 47-kDa antigen were subjected to sodium dodecyl sulfate-polyacrylamide gel electrophoresis (SDS-PAGE) according to the method of Hunkapiller et al. (26). The HA-cleaved protein was then transferred to Millipore polyvinylidene difluoride (PVDF) membrane according to the method of Matsudaira (27). The three resulting peptide bands were cut out and subjected to N-terminal amino acid sequencing (below).

Amino acid sequencing of the native 47-kDa antigen. Approximately 100 pmoles of the 47-kDa protein were subjected to polyacrylamide gel electrophoresis (26) and then transferred to Whatman GF/C glass fiber filter paper derivatized with amino propyl groups according to the method of Aebersold et al. (28) as modified by Yuen et al. (29). N-terminal amino acid sequencing was performed on an Applied Biosystems Model 470A Gas Phase Sequencer coupled to an on-line Model 120A high performance liquid chromatograph (HPLC). Attempts to sequence the N-terminus of the intact 47-kDa protein were unsuccessful. CNBr digestion of the apparently blocked protein immobilized on the glass fiber sequencer filter gave rise to a mixture of peptides from which phenylthiohydantoin (PTH) amino acids could be identified by automated Edman degradation.

Approximately 500 pmoles of the 47-kDa protein were transferred from a 12.5% SDS-PAGE gel to nitrocellulose paper for solid phase tryptic digestion according to the method of Aebersold et al. (30). Peptides were separated by reverse-phase HPLC on an Applied Biosystems Model 130A HPLC using a Brownlee RP300 (2.1×100 mm) C8 column. Separation was performed in 0.1% trifluoroacetic acid using a gradient of 0 to 50% acetonitrile over a duration of 120 minutes, at a flow rate of 50 ul/minute. Peaks were collected manually onto 1 cm discs of Whatman GF/C paper. Cysteine residues were then reduced and alkylated according to the method of Andrews and Dixon (31). Peptides were sequenced directly on an Applied Biosystems Model 470A Sequencer.

DNA sequencing of the 47-kDa antigen gene. Selected DNA fragments were ligated to M13mp18 and used to transfect JM 101 cells. Recombinant phages were identified as white plaques on LB plates containing isopropyl-beta-D-thiogalactopyranoside (IPTG) and X-gal (5-bromo-4-chloro-3-indolyl-b-galactoside). The orientations of the inserts were determined by restriction enzyme mapping of the replicative forms of the phage DNA. Single-stranded phage DNAs were purified from the culture supernatants (32). DNA sequences were determined by the dideoxynucleotide chain termination method (33). For most sequencing reactions, the 17 base universal primer (Bethesda Research Laboratory, Bethesda, Md.) and the Klenow fragment of DNA polymerase I were used. Three oligonucleotides, CATGGTTGACAGCGAGG, CCTCGCTGTCAACCATG, and CATTACCCGCCAAAAGCACG, corresponding to nucleotide positions 471 to 487, 487 to 471, and 166 to 147 of the 47-kDa antigen gene (SEQ ID No:1), respectively, were synthesized in a Model 380B Applied Biosystems oligonucleotide synthesizer and were used for additional sequencing reactions. In some cases, reverse transcriptase was used instead of the Klenow enzyme. The reaction products were subjected to electrophores is on standard 6% or 8% polyacrylamide sequencing gels containing 7.8M urea or on 4–8%, 4–10% or 6–10% polyacrylamide gradient gels with 40% formamide to increase resolution.

Computer analyses. Beckman MicroGenie™ software (Beckman Instruments, Palo Alto, Calif.) (34) was used for DNA sequence analysis.

RESULTS

Subclones of the 47-kDa antigen gene. The various subclone derivatives of the 47-kDa antigen gene and the relevant expression products of these derivatives are shown in FIG. 1. All subclones originated from pNC81 which contains the entire 47-kDa antigen gene and its regulatory region. The first (leftward) PstI site of the D fragment of pNC81 (FIG. 1; nucleotides 1–6 of SEQ ID NO:1) is located 5' to the GC tail used in the original construction of pNC81. Additional PstI recognition sites are located between nucleotides 37–42 and 1139–1144 of SEW ID NO:1. Not shown in FIG. 1 is the location of an ApaI site (GGGCCC), nucleotides 6–83 of SEQ ID NO:1, that presumably was constructed fortuitously as a result of the GC tailing method. Cleavage by ApaI leaves the GC tail attached to the cloning vector. Plasmid constructions lacking the PstI D fragment (e.g., pPH47.1) failed to express any derivative of the 47-kDa antigen. The addition of an active promoter at the XhoII site (upstream from the structural gene) could restore expression of some of the 47-kDa antigen (e.g., pPH47.7). Thus, the 78 base pair PstI D fragment, nucleotides 6–83 of SEQ ID NO:1, contained a region that is required for the expression of the complete 47-kDa antigen gene. Additional restriction enzyme recognition sites in SEQ ID NO:1 were identified as follows: an XhoII site between nucleotides 186–191, Hind II sites between nucleotides 445–450 and 1144–1149, a KpnI site between nucleotides 709–714, a ClaI site between 1072–1077, a HindIII site between nucleotides 1171–1176, and an EcoRI site between nucleotides 1267–1272.

Figure 2:
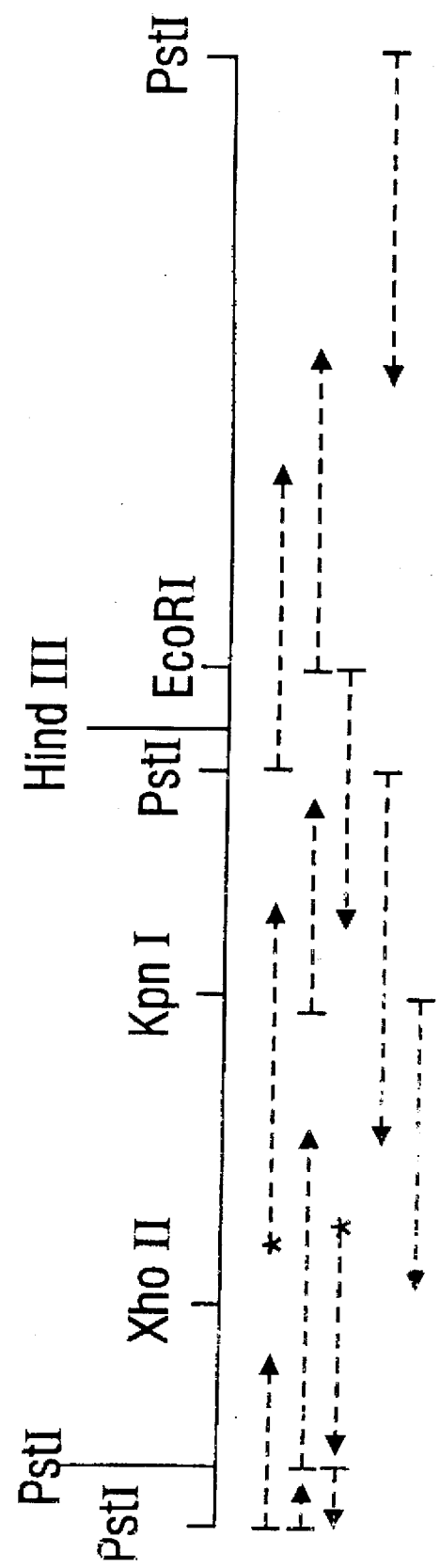
FIG. 2. DNA sequencing strategy for the 47-kDa antigen gene. Restriction enzyme fragments were subcloned into bacteriophage M13 and were sequenced by the dideoxy chain termination method. Arrows below the restriction map indicate the direction and extent of sequencing. Either a universal 17 base primer (bar) or custom synthesized oligonucleotides (*) complementary to the 47-kDa antigen gene sequence were used for sequencing reactions.

DNA sequencinq. The complete nucleotide sequence was obtained by DNA sequencing analysis of subclones shown in FIG. 1. The DNA sequencing strategy used is outlined in FIG. 2; virtually all of the DNA encoding the structural gene for the 47-kDa antigen was sequenced in both directions. Using computer analysis, an open reading frame large enough to represent the 47-kDa antigen (SEQ ID NO:2) was identified which was compatible with genetic expression data for selected subclones.

Gene expression data also established the direction of transcription (11, 23), and the proper codon reading frame was confirmed by amino acid sequencing of trypsin and HA fragments of the native 47-kDa antigen isolated from *T. pallidum*. Edman degradation and HA cleavage yielded peptides that corresponded to the following amino acid positions of SEQ ID NO:2: 84–96, 126–143, 207–221, 266–298, 340–350, 366–390, and 392–414. The two HA cleavage sites were located between nucleotide positions 618 and 619 and positions 1077 and 1078 of SEQ ID NO:1. The combined data suggest that translation is initiated at the first GTG codon (valine) of the reading frame shown in SEQ ID NO:1 as nucleotide position 43, but initiation at a second GTG codon, separated from the first GTG codon by only a single AAA codon, cannot be ruled out at this time. The GTG codon is an acceptable initiation codon for fMethionine in prokaryotes (19). The first GTG codon is preceded by a putative Shine-Dalgarno ribosome binding site (GGAGG) at position −8 to −12 in the DNA sequence. Potential −10 and −35 promoter consensus sequences were not readily identifiable within the 5' untranslated region, although the 15 nucleotide long GC "tail" used in the original cloning strategy (Norgard and Miller, Infect. Immun. 42:435–445, 1983) may have provided some type of promoter activity. In any event, expression of the 47-kDa antigen controlled by this region of the DNA is consistent with other gene expression data which revealed that removal of the 78 base pair Pst I fragment (located in this region) (e.g., subclone pPH47.1) prevents expression of the 47-kDa antigen.

The first GTG codon is followed by a hydrophobic 20 amino acid sequence that Contains a positive charge near its N-terminus (Lys at amino acid positions 2 and 4 of SEQ ID NO:2) characteristic of signal peptides. Furthermore, this first 20 amino acid region terminates with the amino acid sequence Val-Val-Gly-Cys, which is an acceptable signal peptidase II processing site for bacterial lipoproteins (52). This is consistent with the preliminary findings of the inventor that the 47-kDa antigen of T. pallidum contains covalently attached fatty acids when the organism is incubated in vitro with tritiated palmirate. Thus, it is plausible that the 47-kDa antigen is generated by conventional bacterial lipoprotein synthesis pathways (52), which includes processing (removal) of the first 19 amino acids, leaving an N-terminal Cys at position 20 which possesses one amide-linked fatty acid and a thioether-linked diacylglycerol (52).

The combined data strongly support that the 47-kDa antigen is a lipoprotein that is synthesized as a precursor with a 19 amino acid leader peptide which is removed to yield a mature molecule.

The structural gene for the 47-kDa antigen is localized to a 1.3 kb fragment at the most leftward (5') portion of the 2.85 kb DNA insert of pNC81. Therefore, sequence analysis commenced at the 5' PstI insertion site and was performed for approximately 2.9 kb to ensure that the entire 47-kDa structural gene was sequenced. The 3' encoding region of the gene contains two stop codons separated by nine amino acid codons, beginning at positions 1303 and 1333 of SEQ ID NO:1. If the first stop codon is used, the protein possesses a molecular weight of 45,756 (no4 including post-translational modification).

While it is probable that the first TAG stop codon represents the principal stop signal for the termination of translation, the existence of the second TAA stop codon, however, may explain a peculiar phenomenon previously reported; namely, the 47-kDa antigen typically migrates as a 47–48-kDa "doublet" on SDS-PAGE gels (23). Occasionally, termination may fail at the first TGA stop codon, thereby allowing the protein to be elongated an additional 10 amino acids. The 47-kDa molecular weight species of the 47-48-kDa doublet (i.e., to the first stop codon) represents by far the major component. The hypothesis therefore is consistent with the observation of the relevant abundance of the two molecular weight derivatives observed on SDS-PAGE gels.

Figure 3:
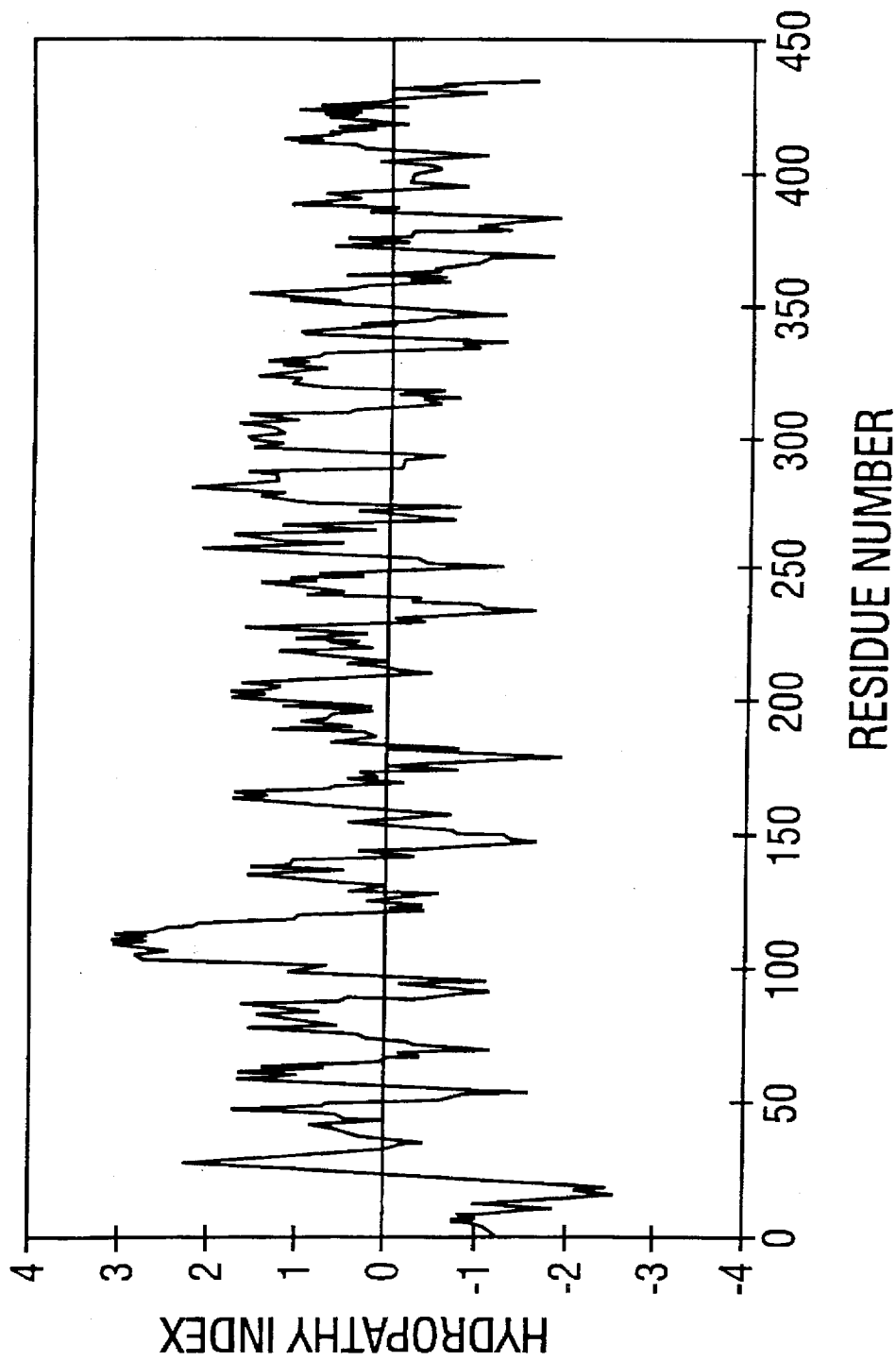
FIG. 3. Hydrophilicity analysis of the 47-kDa amino acid sequence. Note the prominent hydrophobic domain near the N-terminus of the molecule.
Figure 4A:
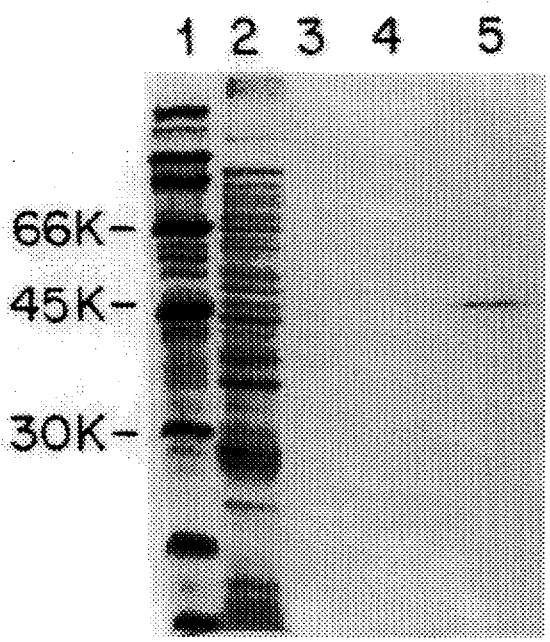
FIG. 4A and FIG. 4B. Immunoaffinity chromatography of the 47-kDa antigen from E. coli pGP1-2-pNC82 cell envelopes. Coomassie brilliant blue-stained SDS-PAGE gel (A) and Western blot with monoclonal antibody 11E3(B). Lanes 1, Molecular mass (MW) standards; lanes 2, pooled, non-absorbed proteins combined with 1% n-octylglucoside washes; lanes 3, 0.5 M MgCl$_2$ wash prior to elution; lanes 4, blank; lanes 5, 47-kDa (47K) antigen eluted from the affinity column.
Figure 4B:
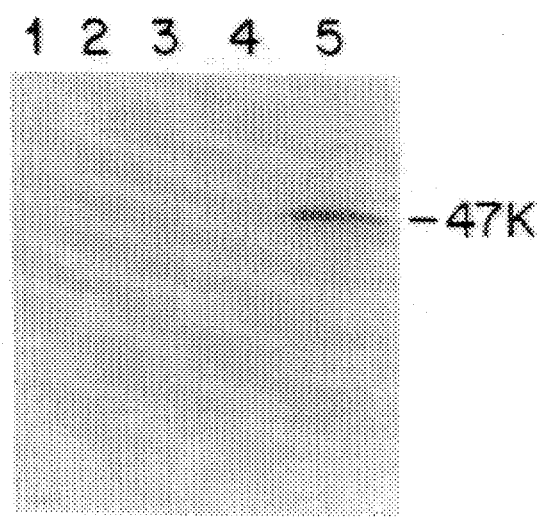

The data disclosed by the present invention provide the molecular basis for elucidation of the respective roles of humoral and cell-mediated immune responses and the immunogenicity of the protein during infection by T. pallidum. Hydrophilicity analysis revealed at least one major hydrophobic domain near the N-terminus (leader peptide) of the precursor molecule. However, several hydrophilic domains of the mature molecule FIG. 3 have been identified as likely important immunogenic/epitopic regions.

The N-terminal regions (amino acids 92 to 119) represent a primary immunodominant epitope. In support of this, preliminary epitope mapping experiments showed that a vast majority of mouse monoclonal antibodies raised against the 47-kDa antigen react with the N-terminal hydroxylamine cleavage fragment containing this hydrophilic domain; the same was true when human syphilitic 'r rabbit anti-T. pallidum sera were examined for antibody reactivity with the hydroxylamine cleavage fragments of the 47-kDa antigen. The protein additionally may contain domain(s), particularly the N-terminal lipopeptide, that serve as polyclonal activators of B lymphocytes (49). This may partially explain the intense and specific fetal IgM response to the 47-kDa antigen in congenital syphilis (7). In addition, certain domains may serve as functional T cell recognition epitopes (50,51) that promote the activity of cell-mediated immunity in the clearance of T. pallidum from early primary lesions (2) and/or during other stages of the pathogenesis process.

There is no doubt that the 47-kDa antigen is an integral membrane protein (23,54), but the actual basis for the hydrophobic character of the molecule is not readily apparent from its primary amino acid sequence. Its characteristic partitioning into the detergent phase upon Triton X-114 extraction (20,23,59) further substantiates its overall hydrophobic nature. Preliminary data derived from radiolabeling experiments with 3H palmitate or oleate suggest that the 47-kDa antigen is covalently modified with lipid. This is consistent with the existence in the amino acid sequence of Val-Val-Gly-Cys at positions 17–20, which represents a plausible consensus sequence for the lipoprotein-specific signal peptidase II of prokaryotes (52). This serves to explain not only the intrinsic hydrophobic character of the 47-kDa antigen, but also the profound immunogenicity of the molecule, inasmuch as lipids confer immunogenicity to proteins.

Monoclonal antibodies directed against the 47-+Da antigen of T. pallidum agglutinate T. pallidum-coated erythrocytes in the microhemagglutination assay for T. pallidum antibodies (MBA-TP test) (4). It was proposed that this efficient agglutination by a monoclonal, antibody was facilitated either by the presence of an abundant 47-kDa antigen among T. pallidum and/or the presence of a repetitive epitope within the antigen. On the basis of sequence data provided herein, the former explanation would appear to be correct. No significant primary repeat epitopes were detected in the DNA and/or amino acid sequences of the 47-kDa antigen. This finding is consistent with our previous contention that the 47-kDa protein of T. pallidum is, indeed, an abundant antigen of the organism (4).

The availability of the entire sequence for the 47-kDa antigen provides additional practical tools. The entire DNA sequence or strategic constituent oligonucleotide portions, including synthetic oligonucleotides, may be used as molecular gene probes for the detection of the organism in various tissues and/or body fluids. Moreover, knowledge of the amino acid sequence allows the preparation of strategic synthetic peptides for use as the basis for improved treponemal serologic tests and/or treponemal synthetic peptide vaccines (53).

EXAMPLE II

Improved Production of the 47-kDa Antigen by Recombinant Means

E. coli derivatives containing plasmids pNC81 or pMN23 express an amount of the 47-kDa antigen that is less than ideal for commercial production. For this reason, a T7 expression vector system was used in an attempt to increase 47-kDa antigen production by recombinant E. coli (56). The 2.85-kb T. pallidum DNA insert from pNC81 was ligated into pT7-6 to create pNC82, which was used to transform E. coli strains K38 or RR1, both of which harbored pGP1-2 (pGP1-2 is disclosed in Ref. 56, pGP1-2 encodes T7 RNA polymerase Under the control of a temperature-sensitive repressor acting on the $P_L$ promoter of bacteriophage lambda). When expression of the 47-kDa antigen was compared between *E. coli* harboring pNC81 and *E. coli* harboring pGP1-2-pNC82 by Western blot analysis, a greater than 20-fold increase (on a per cell basis) in antigen production was found in the expression vector system for *E. coli* K38, or a 100-fold increase was found for *E. coli* RR1. The specific procedure employed for preparing pNC82 is shown immediately below.

Cloning into the expression vector pT7-6. A partial PstI digestion of pNC81 was subjected to electrophoresis on a 1% low-melting-point agarose gel (Bethesda Research Laboratories, Bethesda, Md.). The portion of the gel containing the 2.85-kb PstI fragment (encoding the 47-kDa antigen) was excised and melted at 65° C. The DNA was harvested by column chromatography (Elutip; Schleicher & Schuell (57), followed by standard ethanol precipitation. Plasmid pT7-6 was digested with PstI, treated with alkaline phosphatase, and then ligated to the 2.85-kb fragment of pNC81 to create pNC82. *E. coli* K38 or RR1 containing pGP1-2 was transformed with pNC82; transformants were selected on agar plates containing ampicillin and kanamycin at 50 ug/ml each, and then the clones were tested by the radioimmunocolony blot (RICB) assay for 47-kDa antigen production (11; assay using monoclonal antibody 11E3).

EXAMPLE III

Purification of Recombinant 47-kDa Antigen from *E. coli* cells

Preparation of Cell Envelopes. As a first step in the purification of the recombinant 47-kDa antigen, cell envelopes were prepared from *E. coli* recombinant derivatives containing both pGP1-2 and pNC82 (pGP1-2-pNC82), in that a large majority of the antigen was detected in the cell envelope fraction. Recombinant *E. coli* cells were grown at 37° C. in broth with the appropriate antibiotics to maintain selective pressure on the plasmids. *E. coli* cells containing pGP1-2-pNC82 were induced for 30 min at 42° C. and grown for an additional 3 hrs at 37° C. prior to fractionation. Cells were harvested by centrifugation at 16,270×g for 10 min (4° C.), and the pellets were suspended in a one-fifth volume of 10% (wt/vol) sucrose-20 mM Tris hydrochloride (pH 8.0)-1 mM EDTA (STE buffer) at 0° C. The cells were again harvested by using similar centrifugation conditions and were suspended in 1/50 of the original volume of STE. They were then frozen in liquid nitrogen. The cells were thawed at 37° C. and lysozyme crystals were added to a final concentration of 0.2 mg/ml. After 45 min of 0° C., cells were frozen and thawed twice to create cell envelopes.

Washed cell envelopes of *E. coli* were extracted with 2% Sarkosyl to produce a soluble, cytoplasmic membrane-enriched fraction. SDS-PAGE and Western blot analysis of the Sarkosyl-soluble and -insoluble material from pNC81 indicated that virtually all of the recombinant 47-kDa antigen was solubilized. In contrast, similar analysis of *E. coli* harboring pGP1-2-pNC82 revealed that a significant amount of the 47-kDa protein remained in the Sarkosyl-insoluble, outer membrane-enriched material.

Detergent solubilization of the recombinant form of the 47-kDa antigen from *E. coli*. To determine the optimal solubilization conditions for the recombinant 47-kDa antigen, cell envelopes from *E. coli* pGP1-2-pNC82 were incubated with a variety of ionic and nonionic detergents at different detergent to protein ratios.

In particular, cell envelopes containing 200 mg of total protein in 20 ml were incubated for 1 hr at 4° C. in 0.01, 0.03, 0.1, 0.3, 1.0, and 3.0% NP-40, n-octylglucoside, Sarkosyl, or CHAPS. Relatively insoluble outer membrane-enriched material was collected by centrifugation at 110,000×g for 1 hr at 4° C. The resultant supernatants were analyzed by Western blots with monoclonal antibody 11E3. Results from these experiments are summarized in Table 1. The 47-kDa antigen was solubilized with concentrations of CHAPS and n-octylglucoside as low as 0.01%. Solubilization in Sarkosyl required a detergent concentration of 0.03%, while the 47-kDa protein was least efficiently solubilized by NP-40.

TABLE 1

Solubilization of the recombinant 47-kDa antigen from *E. coli* pGP1-2-pNC82 cell envelopes by using ionic and nonionic detergents

| | Solubilization at the following % of detergent used to detergent solubilize the 47-kDa antigen[a]: | | | | | |
|---|---|---|---|---|---|---|
| | 0.01 | 0.03 | 0.1 | 0.3 | 1.0 | 3.0 |
| CHAPS (wt/vol) | + | + | + | + | + | + |
| n-Octylglucoside (wt/vol) | + | + | + | + | + | + |
| Sarkosyl (wt/vol) | − | + | + | + | + | + |
| NP-40 (vol/vol) | − | − | − | − | + | + |

[a]Symbols; +, visible 47-kDa antigen in 50 ul of resulting supernatant when Western blotted with monoclonal antibody 11E3; −, no visible 47-kDa antigen in 50 ul of resulting supernatant when Western blotted with monoclonal antibody 11E3.

Triton X-114 extraction of *E. coli* cell envelopes from pGP1-2-pNC82. Localization of the recombinant 47-kDa protein to the *E. coli* cell envelope and the requirement for detergent to solubilize the 47-kDa antigen demonstrated the hydrophobic nature of the protein. This was investigated further by using Triton X-114 phase partitioning (58) as a means of assisting in purifying the recombinant antigen.

Cell envelopes from pGP1-2-pNC82-transformed *E. coli* were incubated for 1 hr at 4° C. in 2% Triton X-114 at a protein to detergent ratio of 1:5. Insoluble material was removed by centrifugation at 14,000×g for 15 min in a microcentrifuge. Detergent and aqueous phases were separated by placing tubes at 30° C. for 5 min, followed by centrifugation at 5,800×g for 5 min (room temperature) over 0.25 ml of a 0.25M sucrose cushion. Detergent and aqueous phases were analyzed by Western blotting with anti-47-kDa monoclonal antibody, revealing that the majority of extractable 47-kDa protein segregated into the detergent phase.

Purification of the 47-kDa antigen from *E. coli* by detergent extraction, immunoaffinity chromatography, and chromatofocusing. The foregoing studies demonstrated that, in general, Sarkosyl or Triton X-114 detergent extractions were the preferred methods for solubilizing the 47-kDa antigen from recombinant cells. Thus, the general strategy of detergent solubilization followed by antibody immunoaffinity chromatography was utilized to purify the 47-kDa antigen from *E. coli*. Cell envelopes from pGP1-2-pNC82 transformants (expression vector system) were incubated in 50 mM Tris-hydrochloride (pH 8.0)+0.15M KCl (TK buffer) containing 2% Sarkosyl for 1 hr at 4° C. Insoluble material was removed by centrifugation at 110,000×g (4° C.) for h hr. Prior to this, a monoclonal antibody affinity column was prepared as follows:

Monoclonal antibody 11E3 was dialyzed in 0.1M borate buffer (pH 8.5). A total of 1 ml of matrix (ReactiGel 6X; Pierce Chemical Co., Rockford, Ill.) was added to 1 ml of dialyzed monoclonal antibody (3 mg/ml) for 30 hr at 4° C. The resulting column was washed with four bed volumes of TK buffer containing 1% n-octylglucoside followed by a four-bed-volume wash with 3M guanidine hydrochloride-1% n-octylglucoside-25 mM Tris hydrochloride (pH 8.0)-0.075M KCl.

A "cocktail" of monoclonal antibodies directed against different epitopes of the 47-kDa antigen or monospecific polyclonal antibodies also could be used to prepare the affinity column. The detergent extract of cell envelopes (in solution) was placed with a 1.5 ml batch of monoclonal antibody 11E3 bound to matrix for about 18 hr (overnight) at 4° C. The matrix was washed 3 times with four bed volumes of 1% n-octylglucoside in TK buffer, followed by washing 4 times in four bed volumes of 1% n-octylglucoside-0.5M MgCl$_2$ in TK buffer. The 47-kDa antigen was eluted from the matrix by using four bed volumes of 3M guanidine hydrochloride (pH 8.0)-1% n-octylglucoside-0.5 TK buffer.

The eluted material consisted of the 47-kDa antigen purified to near homogeneity (FIG. 5A and B, lane 5). Silver periodate staining of the eluted material did, however, reveal the presence of minor protein contaminants with molecular masses greater than 47-kDa, but no lipopolysaccharide was detectable. Contaminants could be removed by using a chromatofocusing column and collecting the 47-kDa antigen during elution from the column with polybuffer in fractions with a pH of 4.6 to 4.9. Approximately 34 ug of the 47-kDa antigen was recovered from a starting quantity of about 5.5 mg of Sarkosyl-solubilized *E. coli* cell envelopes.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting in kind or amount of the biological action. Furthermore, other alterations can be introduced, such as the removal of acylation sites (e.g., Cys-20), to produce analogs having numerous useful characteristics. All such modifications are intended to be included within the scope of the appended claims.

REFERENCES

The references which are listed below are hereby incorporated by reference.

1. Norris, S. J., J. F. Alderete, N. H. Axelsen, M. J. Bailey, S. A. Baker-Zander, J. B. Baseman, P. J. Bassford, R. E. Baughn, A. Cockayne, P. A. Hanff, P. Hindersson, S. A. Larsen, M. A. Lovett, S. A. Lukehart, J. N. Miller, M. A. Moskophidis, F. Muller, M. V. Norgard, C. W. Penn, L. V. Stamm, J. D. van Embden, and K. Wicher (1987). Identity of *Treponema pallidum* ssp. pallidum polypeptides: correlation of sodium dodecyl sulfate-polyacrylamide gel electrophoresis results from different laboratories. Electrophoresis 8:77–92.
2. Sell, S., and S. J. Norris (1983). The biology, pathology, and immunology of syphilis. Int. Rev. Exp. Pathol., 24.:203–276.
3. Bishop, N. H., and J. N. Miller (1976). Humoral immunity in experimental syphilis. II. The relationship of neutralizing factors in immune serum to acquired resistance. J. Immunol., 117:197–207.
4. Jones, S. A., K. S. Marchitto, J. N. Miller, and M. V. Norgard (1984). Monoclonal antibody with hemagglutination, immobilization, and neutralization activities defines an immunodominant, 47,000 mol wt., surface-exposed immunogen of *Treponema pallidum* (Nichols). J. Exp. Med., 160:1404–1420.
5. Baker-Zander, S. A., E. W. Hook, P. Bonin, H. H. Handsfield, and S. A. Lukehart (1985). Antigens of *Treponema pallidum* recognized by IgG and IgM antibodies during syphilis in humans. J. Infect. Dis., 151:264–272.
6. Hanff, P. A., T. E. Fehniger, J. N. Miller, and M. A. Lovett (1982). Humoral immune response in human syphilis to polypeptides of *Treponema pallidum*. J. Immunol., 129:1287–1291.
7. Dobson, S. R. M., L. H. Taber, and R. E. Baughn (1988). Recognition of *Treponema pallidum* antigens by IgM and IgG antibodies in congenitally infected newborns and their mothers. J. Infect. Dis., 157:903–910.
8. Hook, E. W., R. E. Roddy, S. A. Lukehart, J. Hom, K. K. Holmes, and M. R. Tam. (1985). Detection of *Treponema pallidum* is lesion exudate with a pathogen-specific monoclonal antibody. J. Clin. Microbiol., 22:241–244.
9. Lukehart, S. A., M. R. Tam, J. Hom, S. A. Baker-Zander, K. K. Holmes, and R. C. Nowinski (1985). Characterization of monoclonal antibodies to *Treponema pallidum*. J. Immunol., 134:585–592.
10. Marchitto, K. S., C. K. Selland-Gossling, and M. V. Norgard (1986). Molecular specificities of monoclonal antibodies directed against virulent Treponema pallidum. Infect. Immun., 51:168–176.
11. Norgard, M. V., N. R. Chamberlain, M. A. Swancutt, and M. S. Goldberg (1986). Cloning and expression of the major 47-kilodalton surface immunogen of Treponema pallidum in *Escherichia coli*. Infect. Immun., 54.:500–506.
12. Norgard, M. V., C. K. Selland, J. R. Kettman, and J. N. Miller (1984), Sensitivity and specificity of monoclonal antibodies directed against antigenic determinants of *Treponema pallidum* (Nichols) in the diagnosis of syphilis. J. Clin. Microbiol., 20:711–717.
13. Romanowski, B., E. Forsey, E. Prasad, S. Lukehart, M. Tam, and E. W. Hook, III (1987). Detection of Treponema pallidum by a fluorescent monoclonal antibody test. Sex. Trans. Dis., 14:156–159.
14. Baker-Zander, S. A., and S. A. Lukehart (1983). Molecular basis of immunological cross-reactivity between *Treponema pallidum* and *Treponema pertenue*. Infect. Immun., 42:634–638.
15. Baker-Zander, S. A., and S. A. Lukehart (1984). Antigenic cross-reactivity between Treponema pallidum and other pathogenic members of the family Spirochaetaceae. Infect. Immun., 46:116–121.
16. Lukehart, S. A., S. A. Baker-Zander, and E. R. Gubish, Jr. (1982). Identification of Treponema pallidum antigens: comparison with a nonpathogenic treponeme. J. Immunol, 129:833–838.
17. Marchitto, K. S., S. A. Jones, R. F. Schell, P. L. Holmans, and M. V. Norgard (1984). Monoclonal antibody analysis of specific antigenic similarities among pathogenic *Treponema pallidum* subspecies. infect. Immun., 45:660–666.
18. Fohn, M. J., F. S. Wignall, S. A. Baker-Zander, and S. A. Lukehart (1988). Specificity of antibodies from patients with pinta for antigens of *Treponema pallidum* subspecies pallidum. J. Infect. Dis., 157:32–37.
19. Norgard, M. V., and J. N. Miller (1983). Cloning and expression of Treponema pallidum (Nichols) antigen genes in *Escherichia coli*. Infect. Immun., 42:435–445.

20. Radolf, J. D., and M. V. Norgard (1988). Pathogen-specificity of *Treponema pallidum* subsp. pallidum integral membrane proteins identified by phase partitioning with Triton X-114. Infect. Immun., 56:1825–1828.
21. Yanisch-Perron, C., J. Vieira, and J. Messing (1985). Improved M13 phage cloning vectors and host strains: nucleotide sequences of the M13mp18 and pUC19 vectors. Gene, 33:103,119.
22. Messing, J. (1979). A multipurpose cloning system based on the single-stranded DNA bacteriophage M13. Rec. DNA Tech. Bull., 2:43–48.
23. Chamberlain, N. R., J. D. Radolf, P. L. Hsu, S. Sell, and M. V. Norgard (1988). Genetic and physicochemical characterization of the recombinant DNA-derived 47-kilodalton surface immunogen of *Treponema pallidum* subsp. pallidum. Infect. Immun., 56:71–78.
24. Bordier, C. (1981). Phase separation of integral membrane proteins in Triton X-114 solution. J. Biol. Chem., 256:1604–1607.
25. Bornstein, P., and G. Balain (1977). Cleavage at Asn-Gly bonds with hydroxylamine. Meth. Enzymol., 47:132–145.
26. Hunkapiller, M. W., E. Lujan, F. Ostrander, and L. E. Hood (1983). Isolation of microgram quantities of protein from polyacrylamide gels for amino acid sequence analysis. Meth. Enzymol., 91:227–236.
27. Matsudaira, P. (1987). Sequence from picomole quantities of proteins electroblotted onto polyvinylidene difluoride membranes. J. Biol. Chem., 262:10035–10038.
28. Aebersold, R. H., B. T. David, L. E. Hood, and S. B. H. Kent (1986). Electroblotting onto activated glass. J. Biol. Chem., 261:4229–4238.
29. Yuen, S., M. W. Hunkapiller, K. J. Wilson, and P. M. Yuan. "SDS-PAGE electroblotting." Applied Biosystems User Bulletin, Protein Sequencer, Issue #25. Nov. 18, 1986.
30. Aebersold, R. H., J. Leavitt, R. A. Saavedra, L. E. Hood, and S. B. H. Kent (1987). Internal amino acid sequence analysis of proteins separated by one- or two-dimensional gel electrophoresis by in situ protease digestion on nitrocellulose. Proc. Natl. Acad. Sci. USA, 84:6970–6974.
31. Andrews, P. C., and J. E. Dixon (1987). A procedure for in situ alkylation of cysteine residues on glass fiber prior to protein microsequence analysis. Anal. Biochem., 161:524–528.
32. Messing, J. (1983). New M13 vectors for cloning. Meth. Enzymol., 101:20–78.
33. Sanger, F., S. Nicklen, and A. R. Coulson (1977). DNA sequencing with chain-terminating inhibitors. Proc. Natl. Acad. Sci. USA, 74:5463–5467.
34. Queen, C., and L. J. Korn (1984). A comprehensive sequence analysis program for the IBM personal computer. Nucl. Acids Res., 12:581–599.
35. Miao, R., and A. H. Fieldsteel (1978). Genetics of Treponema: relationship between *Treponema pallidum* and five cultivable treponemes. J. Bacteriol., 133:101–107.
36. Hopp, T. P., and K. R. Woods (1981). prediction of protein antigenic determinants from amino acid sequences. Proc. Natl. Acad. Sci. USA, 78:3824–3828.
37. Kyte, J., and R. F. Doolittle 91982). A simple method for displaying the hydrophatic character of a protein. J. Mol. Biol., 157:105–132.
38. Boak, R. A., Carpenter, C. M., Miller, J. N., Drusch, H. E., Chapman, J. M., and Heidbreder, G. A., Biologic false positive reactions for syphilis in pregnancy as determined by the *Treponema pallidum* immobilization test. Surg. Gyn Obst., 101:751 (1955).
39. Grossman, L. J., and Pecry, T. M., Biologically false-positive serologic tests for syphilis due to smallpox vaccination. Amer. J. Clin. Path., 51:375 (1969).
40. Rockwell, D. H., Yobs, A. R., and Moore, M. B., The Tuskegee study of untreated syphilis. The 30th year of observation. Arch. Intern. Med., 114:792 (1964).
41. Buchanon, C. S., and Haserick, J. R., FTA-ABS test in pregnancy: A probable false-positive reaction. Arch. Derm. (Chicago), 102:322 (1970).
42. Kraus, S. J., Haserick, J. R., and Lantz, M. A. Fluorescent treponemal antibody-absorption test reactions in lupus erythematosis. A typical beading pattern and probable false positive reactions. New Eng. J. Med., 282:1287 (1970).
43. Mackey, D. M., Price, E. V., Knox, J. M. and Scotti, A. T., Specificity of the FTA-ABS test for syphilis. An evaluation. JAMA, 207:1683 (1969).
44. Blum, G., Ellner, P. D., McCarthy, L. R., and Papachristos, T., Reliability of the treponemal hemagglutination test for the serodiagnosis of syphilis. J. Infect. Dis., 127:321 (1973).
45. Ghinsberg, R., Elian, M., and Stanic, G., Specificity and sensitivity of the *Treponema pallidum* hemagglutination test in syphilitic and non-syphilitic sera. WHO/VDT/RES, 72:289 (1972).
46. Baker et al. (1988), Infect. Immun., 56:1076–1083.
47. Chase et al. (1986), Infect. Immun., 53:711–712.
48. Gold, L., D. Pribow, T. Schneider, S. Shinedling, B. Swebilius Singer, and G. Stormo. (1981). Translation initiation in prokaryotes. Ann. Rev. Microbiol., 35:365–403.
49. Vordermeier, H. M., and W. G. Bessler (1987). Polyclonal activation of murine B lymphocytes in vitro by *Salmonella typhimurium* porins. Immunobiol., 175:245–251.
50. Berzofsky, J. A., K. B. Cease, J. L. Cornette, J. L. Spouge, H. Margalit, I. J. Berkower, M. F. Good, L. H. Miller, and C. DeLisi (1987). Protein antigenic structures recognized by T cells: potential applications to vaccine design. Immunol. Rev., 98:9–52.
51. Margalit, H., J. L. Spouge, J. L. Cornette, K. B. Cease, C. DeLisi, and J. A. Berzofsky (1987). Prediction of immunodominant helper T cell antigenic sites from the primary sequence. J. Immunol., 138:2213–2229.
52. Wu, H. C. and M. Tokunaga (1986). Biogenesis of lipoproteins in bacterial. Curr. Top. Microbiol. Immunol., 125:127–157.
53. Lerner, R. A., N. Green, A. Olson, T. Shinnick, and J. G. Sutcliffe (1981). The development of synthetic vaccines. Hosp. Prac., 16:55–62.
54. Radolf, J. D., N. R. Chamberlain, A. Clausell, and M. V. Norgard (1988). Identification and localization of integral membrane proteins of virulent *Treponema pallidum* subsp. pallidum by phase partitioning with the nonionic detergent Triton X-114. Infect. Immun., 56:490–498.
55. Robertson, S. M., J. R. Kettman, J. N. Miller, and M. V. Norgard (1982). Murine monoclonal antibodies specific for virulent *Treponema pallidum* (Nichols). Infect. Immun., 36:1076–1085.
56. Tabor, S., and C. C. Richardson (1985). A Bacteriophage T7 RNA polymerase/promoter system for controlled exclusive expression of specific genes. Proc. Natl. Acad. Sci. USA, 82:1074–1078.
57. Schmitt, J. J., and B. N. Cohen (1983). Quantitative isolation of DNA restriction fragments from low-melting agarose by Elutip-d affinity chromatography. Anal. Biochem., 133:462–464.

58. Bordier, C. (1981). Phase separation of integral membrane proteins in Triton X-114 solution. J. Biol. Chem., 256:1604–1607.
59. Adelman et al., (1983), DNA, 2:183.
60. Messing et al., Third Cleveland Symposium on Macromolecules and Recombinant DNA, Editor A. Walton, Elsevier, Amsterdam (1981).
61. Crea et al., (1978) Proc. Natl. Acad. Sci. U.S.A, 75:5765.
62. Bolivar et al., Gene, 2:95 (1977).
63. Chang et al., Nature, 375:615 (1978).
64. Itakura et al., Science, 298:1056 (1977).
65. Goeddel et al., Nature, 281:544 (1979).
66. Goeddel et al., Nucleic Acids Res., 8:4057 (1980).
67. EPO Appl. Publ. No. 0036776.
68. Siebwenlist et al., Cell, 20:269 (1980).
69. Stinchcomb et al., Nature, 282:39 (1979).
70. Kingsman et al., Gene, 7:141 (1979).
71. Tschemper et al., Gene, 10:157 (1980).
72. Jones, Genetics, 85:12 (1977).
73. Hitzeman et al., J. Biol. Chem., 255:2073 (1980).
74. Hess et al., J. Adv. Enzyme Reg., 7:149 (1968).
75. Holland et al., Biochemistry, 17:4900 (1978).
76. Tissue Culture, Academic Press, Kruse and Patterson, editors (1973).
77. Fiers et al., Nature, 273:113 (1978).
78. Horn, J. E., T. Quinn, M. Hammer, L. Palmer, and S. Falkow (1986. Use of nucleic acid probes for the detection of sexually transmitted infectious agents. Diag. Microbiol. Infect. Dis., 4:101S–109S.
79. Moseley, S. L., I. Huq, A. R. M. Alim, M. So, M. Smadpour-Motalebi, and S. Falkow (1980). Detection of enterotoxigenic *Escherichia coli* by DNA colony hybridization. J. Infect. Dis., 142:892–898.
80. Bryan, R. N., J. L. Ruth, R. D. Smith and J. M. LeBon (1986). Diagnosis of clinical samples with synthetic oligonucleotide hybridization probes, p. 112–116. In L. Leive (ed.), Microbiology-1986. American Society for Microbiology, Washington, D.C.
81. Richards et al. (1988), Infect. Immun., 56:682–686.
82. Kersten et al. (1988), Infect. Immun., 56:432–438.
83. Miller, J. N., Value and limitations of nontreponemal and treponemal tests in the laboratory diagnosis of syphilis. Clin. Obst. Gyn., 18:191 (1975).
84. Boak, R. A., Carpenter, C. M., and Miller, J. N., Biologic false positive reactions for syphilis among narcotic addicts. JAMA, 176:326 (1961).

What is claimed is:

1. A purified 47-kDa *T. pallidum* antigen derived from recombinant DNA, said recombinant DNA having a sequence as defined in SEQ ID NO: 1.

2. The 47-dKa antigen of claim 1 substantially free of *T. pallidum* antigens other than sequences encoding the 47-kDa antigen.

3. A purified *T. pallidum* antigen encoded by a sequence of amino acids 1 to 443 of SEQ ID NO: 2.

4. The 47-kDa *T. pallidum* antigen of claim 3 substantially free of *Treponema pallidum* antigens other than the 47-kDa *Treponema pallidum* antigen.

5. The 47-kDa antigen of claim 3 prepared by recombinant expression.

6. The 47-kDa antigen of claim 5 substantially free of *T. pallidum* antigens other than the 47-kDa antigen.

7. A composition comprising purified 47-kDa antigen of *T. pallidum* derived from recombinant DNA, said recombinant DNA having a sequence as defined in SEQ ID NO: 1.

8. A composition comprising purified 47-kDa antigen of *T. pallidum* prepared by recombinant expression and having a sequence as defined in SEQ ID NO:2.

9. A 47-kDa *T. pallidum* antigen free of Cys-20 acylation, said antigen derived from recombinant DNA, said recombinant DNA having a sequence as defined in SEQ ID NO: 1.

10. A purified *T. pallidum* peptide encoded by a sequence of amino acids Val at position 92 to Ser at position 119 of SEQ ID NO: 2.

11. The peptide of claim 10, further defined as: NH2-Val-Leu-Gly-Glu-Lys-Val-Leu-Ser-Lys-Gln-Glu-Thr-Glu-Asp-Ser-Arg-Gly-Arg-Lys-Lys-Trp-Glu-Tyr-Glu-Thr-Asp-Pro-Ser-COOH.

\* \* \* \* \*